United States Patent
Mehrling et al.

(10) Patent No.: US 12,370,177 B2
(45) Date of Patent: *Jul. 29, 2025

(54) COMPOUNDS FOR TREATING BRAIN CANCER

(71) Applicant: Purdue Pharmaceutical Products L.P., Stamford, CT (US)

(72) Inventors: Thomas Jorg Mehrling, Basel (CH); Claudio Festuccia, L'Aquila (IT)

(73) Assignee: Purdue Pharmaceutical Products L.P., Stamford, CT (US)

( * ) Notice: Subject to any disclaimer, the term of this patent is extended or adjusted under 35 U.S.C. 154(b) by 271 days.

This patent is subject to a terminal disclaimer.

(21) Appl. No.: 17/874,621

(22) Filed: Jul. 27, 2022

(65) Prior Publication Data

US 2023/0049350 A1 Feb. 16, 2023

Related U.S. Application Data

(63) Continuation of application No. 15/314,172, filed as application No. PCT/EP2015/056667 on Mar. 26, 2015, now Pat. No. 11,419,853.

(30) Foreign Application Priority Data

May 28, 2014 (GB) ..................... 1409471

(51) Int. Cl.
| | | |
|---|---|---|
| *A61K 31/4184* | (2006.01) | |
| *A61K 31/407* | (2006.01) | |
| *A61K 31/427* | (2006.01) | |
| *A61K 31/502* | (2006.01) | |
| *A61K 31/5377* | (2006.01) | |
| *A61K 31/55* | (2006.01) | |
| *A61K 31/573* | (2006.01) | |
| *A61K 31/58* | (2006.01) | |
| *A61K 31/69* | (2006.01) | |
| *A61K 38/05* | (2006.01) | |
| *A61K 38/06* | (2006.01) | |
| *A61K 39/39* | (2006.01) | |
| *A61K 39/395* | (2006.01) | |
| *A61K 45/06* | (2006.01) | |

(52) U.S. Cl.
CPC ........ *A61K 31/4184* (2013.01); *A61K 31/407* (2013.01); *A61K 31/427* (2013.01); *A61K 31/502* (2013.01); *A61K 31/5377* (2013.01); *A61K 31/55* (2013.01); *A61K 31/573* (2013.01); *A61K 31/58* (2013.01); *A61K 31/69* (2013.01); *A61K 38/05* (2013.01); *A61K 38/06* (2013.01); *A61K 39/3955* (2013.01); *A61K 45/06* (2013.01)

(58) Field of Classification Search
CPC ............. A61K 31/4184; A61K 31/407; A61K 31/427; A61K 31/502; A61K 31/5377; A61K 31/55; A61K 31/573; A61K 31/58; A61K 31/69; A61K 38/05; A61K 38/06; A61K 39/3955; A61K 45/06

See application file for complete search history.

(56) References Cited

U.S. PATENT DOCUMENTS

| | | | |
|---|---|---|---|
| 4,522,811 | A | 6/1985 | Eppstein et al. |
| 5,134,127 | A | 7/1992 | Stella et al. |
| 5,376,645 | A | 12/1994 | Stella et al. |
| 5,571,534 | A | 11/1996 | Jalonen et al. |
| 5,874,418 | A | 2/1999 | Stella et al. |
| 6,046,177 | A | 4/2000 | Stella et al. |
| 6,087,367 | A | 7/2000 | Breslow et al. |
| 6,133,248 | A | 10/2000 | Stella |

(Continued)

FOREIGN PATENT DOCUMENTS

| | | |
|---|---|---|
| CL | 0501-2003 | 3/2003 |
| CL | 2272-2005 | 9/2005 |

(Continued)

OTHER PUBLICATIONS

NCT00823797 (Year: 2009).*
Everhard (Year: 2006).*
Advanced Accelerator Applications, Ongoing Clinical Studies with Advanced Accelerator Applications Pipeline Candidates. Retrieved online at: http://www.adacap.com/research-development/clinical-trials/. 6 pages, (2014).

(Continued)

*Primary Examiner* — Jeffrey S Lundgren
*Assistant Examiner* — Ibrahim D Bori
(74) *Attorney, Agent, or Firm* — McCarter & English, LLP; Yu Lu

(57) ABSTRACT

There is provided a compound of formula I or a pharmacologically acceptable salt thereof:

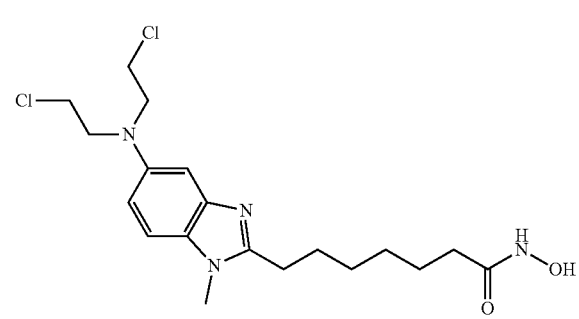

for use in the treatment of a brain cancer selected from a MGMT positive astrocytic brain tumor, a metastatic brain cancer and primary CNS lymphoma and a method of treating said brain cancers in a patient in need thereof comprising administering to the patient said compound of formula I or a pharmacologically acceptable salt thereof.

7 Claims, 19 Drawing Sheets

(56) References Cited

U.S. PATENT DOCUMENTS

| | | |
|---|---|---|
| 6,214,852 B1 | 4/2001 | Kim et al. |
| 6,407,079 B1 | 6/2002 | Muller et al. |
| 8,461,350 B2 | 6/2013 | Brittain et al. |
| 8,609,864 B2 | 12/2013 | Chen et al. |
| 8,962,855 B2 | 2/2015 | Chen et al. |
| 9,096,627 B2 | 8/2015 | Chen et al. |
| 9,376,395 B2 | 6/2016 | Chen et al. |
| RE46,144 E | 9/2016 | Chen et al. |
| 9,889,147 B2 | 2/2018 | Utku |
| 9,993,482 B2 | 6/2018 | Mehrling |
| 10,118,901 B2 | 11/2018 | Chen et al. |
| 10,406,138 B2 | 9/2019 | Mehrling et al. |
| 10,744,120 B2 | 8/2020 | Mehrling et al. |
| 11,266,631 B2 | 3/2022 | Mehrling et al. |
| 11,318,117 B2 | 5/2022 | Mehrling et al. |
| 11,413,276 B2 | 8/2022 | Mehrling |
| 11,419,853 B2 | 8/2022 | Mehrling et al. |
| 11,576,899 B2 | 2/2023 | Mehrling |
| 11,896,583 B2 | 2/2024 | Mehrling |
| 12,048,688 B2 | 7/2024 | Mehrling et al. |
| 12,064,417 B2 | 8/2024 | Mehrling et al. |
| 2002/0076409 A1 | 6/2002 | March et al. |
| 2006/0079528 A1 | 4/2006 | Finn et al. |
| 2006/0159713 A1 | 7/2006 | Brittain et al. |
| 2008/0146556 A1 | 6/2008 | Diebold et al. |
| 2010/0022512 A1 | 1/2010 | Wisdom et al. |
| 2010/0216858 A1 | 8/2010 | Popek et al. |
| 2011/0190363 A1 | 8/2011 | Drager et al. |
| 2011/0269706 A1 | 11/2011 | Chen et al. |
| 2011/0311624 A1 | 12/2011 | Loury et al. |
| 2012/0289570 A1 | 11/2012 | Lengyel et al. |
| 2013/0030237 A1 | 1/2013 | Theuer |
| 2013/0209558 A1 | 8/2013 | Patzak et al. |
| 2014/0303218 A1 | 10/2014 | Chen et al. |
| 2015/0086551 A1 | 3/2015 | Chen et al. |
| 2015/0231198 A1 | 8/2015 | Carniti et al. |
| 2017/0095482 A1 | 4/2017 | Mehrling |
| 2017/0151218 A1 | 6/2017 | Mehrling et al. |
| 2018/0098969 A1 | 4/2018 | Mehrling et al. |
| 2019/0343807 A1 | 11/2019 | Mehrling et al. |
| 2020/0113870 A1 | 4/2020 | Mehrling |
| 2020/0261423 A1 | 8/2020 | Mehrling |
| 2021/0059989 A1 | 3/2021 | Mehrling et al. |
| 2021/0346351 A1 | 11/2021 | Mehrling et al. |
| 2022/0016084 A1 | 1/2022 | Hilgier et al. |
| 2022/0016085 A1 | 1/2022 | Hilgier et al. |
| 2022/0280485 A1 | 9/2022 | Mehrling et al. |
| 2022/0401417 A1 | 12/2022 | Mehrling et al. |
| 2023/0080216 A1 | 3/2023 | Mehrling |
| 2023/0277507 A1 | 9/2023 | Mehrling |
| 2024/0082220 A1 | 3/2024 | Mehrling et al. |
| 2024/0139155 A1 | 5/2024 | Mehrling |
| 2024/0252472 A1 | 8/2024 | Diaz-Tejedor et al. |
| 2024/0261265 A1 | 8/2024 | Mehrling |
| 2024/0316009 A1 | 9/2024 | Mehrling et al. |

FOREIGN PATENT DOCUMENTS

| | | | |
|---|---|---|---|
| CL | 3232-2006 | 11/2006 | |
| CN | 1764648 A | 4/2006 | |
| CN | 101084876 A | 12/2007 | |
| CN | 101928234 A | 12/2010 | |
| CN | 102993102 A | 3/2013 | |
| DE | 34727 A1 | 12/1964 | |
| EP | 0717638 B1 | 3/2002 | |
| EP | 3148529 A1 | 4/2017 | |
| JP | 2007-531793 A | 11/2007 | |
| JP | 2012-515776 A | 7/2012 | |
| KR | 10-2001-0031896 A | 4/2001 | |
| WO | 1991/07950 A1 | 6/1991 | |
| WO | WO-1995/030442 A1 | 11/1995 | |
| WO | WO-2002/010161 A1 | 2/2002 | |
| WO | WO-2002/22577 A2 | 3/2002 | |
| WO | WO-2002/026696 A1 | 4/2002 | |
| WO | WO-2002/055017 A2 | 7/2002 | |
| WO | WO-2004/076386 A2 | 9/2004 | |
| WO | 2005/016859 A2 | 2/2005 | |
| WO | WO-2005/013958 A1 | 2/2005 | |
| WO | WO-2005/097747 A1 | 10/2005 | |
| WO | WO-2006/120456 A1 | 11/2006 | |
| WO | WO-2007/134169 A2 | 11/2007 | |
| WO | WO-2008/050125 A1 | 5/2008 | |
| WO | WO-2008/067027 A2 | 6/2008 | |
| WO | WO-2009/036016 A1 | 3/2009 | |
| WO | WO-2009/067453 A1 | 5/2009 | |
| WO | WO-2009/100045 A1 | 8/2009 | |
| WO | WO-2010/042568 A1 | 4/2010 | |
| WO | WO-2010/075542 A1 | 7/2010 | |
| WO | WO-2010/085377 A2 | 7/2010 | |
| WO | WO-2010/097700 A1 | 9/2010 | |
| WO | WO-2011/017448 A1 | 2/2011 | |
| WO | WO-2013/039488 A1 | 3/2013 | |
| WO | WO-2013040286 A2 * | 3/2013 | ............ A61K 31/16 |
| WO | WO-2013/113838 A1 | 8/2013 | |
| WO | WO-2015/085289 A1 | 6/2015 | |
| WO | WO-2015/180865 A1 | 12/2015 | |
| WO | WO-2015/181154 A1 | 12/2015 | |
| WO | WO-2015/181156 A1 | 12/2015 | |
| WO | WO-2015/181157 A1 | 12/2015 | |
| WO | WO-2016/087950 A1 | 6/2016 | |
| WO | WO-2017/067474 A1 | 4/2017 | |
| WO | 2018/229132 A1 | 12/2018 | |
| WO | 2018/229133 A1 | 12/2018 | |

OTHER PUBLICATIONS

Aguado Bueno et al., Preliminary Experience of the Spanish Compassionate Use Registry of Bendamustine in Patients with Relapsed and/or Refractory Multiple Myeloma. Blood. 2012;120(21), Abstract 4035.

Al-Ani et al., Changes in urinary metabolomic profile during relapsing renal vasculitis. Sci Rep. Dec. 1, 2016;6:38074. 11 pages.

Alfarouk et al., Resistance to cancer chemotherapy: failure in drug response from ADME to P-gp. Cancer Cell Int. Jul. 15, 2015;15:71.

American Cancer Society, How does chemotherapy affect the risk of second cancers? Retrieved online at: https://www.cancer.org/treatment/treatments-and-side-effects/physical-side-effects/second-cancers-in-adults/chemotherapy.html. 5 pages (2017).

Anastasia et al., Bendamustine for Hodgkin lymphoma patients failing autologous or autologous and allogeneic stem cell transplantation: a retrospective study of the Fondazione Italiana Linfomi. Br J Haematol. Jul. 2014;166(1):140-2.

Andersson et al., Discovery of novel drug sensitivities in T-PLL by high-throughput ex vivo drug testing and mutation profiling. Leukemia. Aug. 14, 2017. pp. 1-14.

Andersson et al., Primary T-Prolymphocytic Leukemia (T-PLL) Cells Are Sensitive to BCL-2 and HDAC Inhibitors: Results From High-Throughput Ex Vivo Drug Testing. Blood. 2013;122:3828. 6 pages.

Angelucci et al., Suberoylanilide hydroxamic acid partly reverses resistance to paclitaxel in human ovarian cancer cell lines. Gynecol Oncol. Dec. 2010;119(3):557-63.

Arun et al., The PARP inhibitor AZD2281 (Olaparib) induces autophagy/mitophagy in BRCA1 and BRCA2 mutant breast cancer cells. Int J Oncol. Jul. 2015;47(1):262-8.

Attal et al., Lenalidomide, Bortezomib, and Dexamethasone with Transplantation for Myeloma. The New England Journal of Medicine. Apr. 6, 2017;376:1311-1320.

Audeh et al., Oral poly(ADP-ribose) polymerase inhibitor olaparib in patients with BRCA1 or BRCA2 mutations and recurrent ovarian cancer: a proof-of-concept trial. Lancet. Jul. 24, 2010;376(9737):245-51.

Bachmann et al., Epigenetic silencing of BIM in glucocorticoid poor-responsive pediatric acute lymphoblastic leukemia, and its reversal by histone deacetylase inhibition. Blood. Oct. 21, 2010;116(16):3013-22.

Bagchi, Bendamustine for advanced sarcoma. Lancet Oncol. Aug. 2007;8(8):674.

Baker et al., Investigation of bendamustine HCL in a phase 2 study in women with resistant ovarian cancer. Invest New Drugs. Feb. 2013;31(1):160-6.

(56) References Cited

OTHER PUBLICATIONS

Balfour et al., Bendamustine. Drugs. 2001;61(5):631-8.
Barendsen et al., Inhibition of TPA-induced monocytic differentiation in THP-1 human monocytic leukemic cells by staurosporine, a potent protein kinase C inhibitor. Leuk Res. 1990;14(5):467-74.
Bender, Across the divide. The blood-brain barrier represents a formidable obstacle for cancer drugs. Nature. Sep. 27, 2018;561:S46-S47.
Berenson et al., Phase I/II trial assessing bendamustine plus bortezomib combination therapy for the treatment of patients with relapsed or refractory multiple myeloma. Br J Haematol. Feb. 2013;160(3):321-30.
Bernhard et al., Quality of life and quality-adjusted survival (Q-TWiST) in patients receiving dose-intensive or standard dose chemotherapy for high-risk primary breast cancer. Br J Cancer. Jan. 15, 2008;98(1):25-33.
Besse et al., The first in class, alkylator-histone-deacetylase-inhibitor fusion molecule EDO-S101 in combination with proteasome inhibitors induces highly synergistic pro-apoptotic signaling through UPR activation and suppression of c-Myc and BCL2 in multiple meyloma. ASH, 2016.
Besse et al., The first-in-class alkylating HDAC inhibitor EDO-S101 is highly synergistic with proteasome inhibition against multiple myeloma through activation of multiple pathways. Blood Cancer J. Jul. 2017;7(7):e589. 4 pages.
Besse et al., The First-in-Class, Alkylator-Histone-Deacetylase-Inhibitor Fusion Molecule EDO-S101 in Combination with Proteasome Inhibitors Induces Highly Synergistic Pro-Apoptotic Signaling through UPR Activation and Suppression of c-MYC and BCL2 in Multiple Myeloma. 58th ASH Annual Meeting, San Diego, Dec. 3-6, 2016, Publication No. 4466. 1 page.
Biete et al., Whole abdominal radiotherapy in ovarian cancer. Rep Pract Oncol Radiother. Mar. 23, 2010;15(2):27-30.
Bijnsdorp et al., Analysis of Drug Interactions. Cancer Cell Culture, Methods and Protocols, Second Edition, Methods in Molecular Biology, vol. 731. Ian A. Cree (Ed.), Humana Press. Chapter 34, pp. 421-434, (2011).
Blattmann et al., Enhancement of radiation response in osteosarcoma and rhabdomyosarcoma cell lines by histone deacetylase inhibition. Int J Radiat Oncol Biol Phys. Sep. 1, 2010;78(1):237-45.
Bose et al., Histone deacetylase inhibitor (HDACI) mechanisms of action: emerging insights. Pharmacol Ther. Sep. 2014;143(3):323-36.
Botrugno et al., Molecular pathways: old drugs define new pathways: non-histone acetylation at the crossroads of the DNA damage response and autophagy. Clin Cancer Res. May 1, 2012;18(9):2436-42.
Braga et al., Crystal Polymorphism and Multiple Crystal Forms. Struct Bond. 2009;132:25-50.
Brewster et al., Cyclodextrins as pharmaceutical solubilizers. Adv Drug Deliv Rev. Jul. 30, 2007;59(7):645-66.
Bruce et al., Glioblastoma Multiforme Treatment & Management. Medscape. Retrieved online at: https://emedicine.medscape.com/article/283252-treatment. 20 pages. Jun. 14, 2017.
Buglio et al., Histone deacetylase inhibitors in Hodgkin lymphoma. Invest New Drugs. Dec. 2010;28 Suppl 1:S21-7.
Buglio et al., Vorinostat inhibits STAT6-mediated TH2 cytokine and TARC production and induces cell death in Hodgkin lymphoma cell lines. Blood. Aug. 15, 2008;112(4):1424-33.
Cai et al., Combination of bendamustine and entinostat synergistically inhibits proliferation of multiple myeloma cells via induction of apoptosis and DNA damage response. Cancer Lett. Jul. 28, 2013;335(2):343-50.
Cai et al., Discovery of 7-(4-(3-ethynylphenylamino)-7-methoxyquinazolin-6-yloxy)-N-hydroxyheptanamide (CUDc-101) as a potent multi-acting HDAC, EGFR, and HER2 inhibitor for the treatment of cancer. J Med Chem. Mar. 11, 2010;53(5):2000-9.
Cai et al., Solubilization of vorinostat by cyclodextrins. J Clin Pharm Ther. Oct. 2010;35(5):521-6.

Campos et al., Expression of nuclear receptor corepressors and class I histone deacetylases in astrocytic gliomas. Cancer Sci. Feb. 2011;102(2):387-92.
Chamberlain et al., Salvage therapy with bendamustine for methotrexate refractory recurrent primary CNS lymphoma: a retrospective case series. J Neurooncol. May 2014;118(1):155-62.
Chamberlain et al., Salvage therapy with single agent bendamustine for recurrent glioblastoma. J Neurooncol. Dec. 2011;105(3):523-30.
Chavez et al., Triple negative breast cancer cell lines: one tool in the search for better treatment of triple negative breast cancer. Breast Dis. 2010;32(1-2):35-48.
Chen et al., A 71-gene signature of TRAIL sensitivity in cancer cells. Mol Cancer Ther. Jan. 2012;11(1):34-44.
Chen et al., Dexamethasone and vorinostat cooperatively promote differentiation and apoptosis in Kasumi-1 leukemia cells through ubiquitination and degradation of AML1-ETO. Zhonghua Xue Ye Xue Za Zhi. Sep. 2013;34(9):741-4.
Chen et al., Discovery of a Novel, Efficient, and Scalable Route to Bendamustine Hydrochloride: The API in Treanda. Org Process Res Dev. 2011;15(5):1063-1072.
Chesi et al., Drug response in a genetically engineered mouse model of multiple myeloma is predictive of clinical efficacy. Blood. Jul. 12, 2012;120(2):376-85.
Chesi et al., Identification of Novel Therapeutic Targets in the Clinically Predictive Vk*MYC Mouse Model of Multple Myeloma. ASH, 2 pages. 2014.
Chesi et al., Identification of Novel Therapeutic Targets in the Clinically Predictive Vk*MYC Mouse Model of Multple Myeloma. Blood. 2014;124:415.
Chisholm et al., Emergence of drug tolerance in cancer cell populations: an evolutionary outcome of selection, nongenetic instability, and stress-induced adaptation. Cancer Res. Mar. 15, 2015;75(6):930-9.
Chiu et al., Suberoylanilide hydroxamic acid, an inhibitor of histone deacetylase, enhances radiosensitivity and suppresses lung metastasis in breast cancer in vitro and in vivo. PLoS One. Oct. 10, 2013;8(10):e76340. 12 pages.
Choi et al., Enhanced cytotoxic effect of radiation and temozolomide in malignant glioma cells: targeting PI3K-AKT-mTOR signaling, HSP90 and histone deacetylases. BMC Cancer. Jan. 13, 2014;14:17. 12 pages.
Chou, Drug combination studies and their synergy quantification using the Chou-Talalay method. Cancer Res. Jan. 15, 2010;70(2):440-6.
Chow et al., In vitro induction of apoptosis of neoplastic cells in low-grade non-Hodgkin's lymphomas using combinations of established cytotoxic drugs with bendamustine. Haematologica. May 2001;86(5):485-93.
Ciavatta et al., Epigenetic basis for aberrant upregulation of autoantigen genes in humans with ANCA vasculitis. J Clin Invest. Sep. 2010;120(9):3209-19.
Ciusani et al., Valproic acid increases the in vitro effects of nitrosureas on human glioma cell lines. Oncol Res. 2007;16(10):453-63.
Clinicaltrials.gov, A Phase 1 Study to Investigate the Safety, Pharmacokinetic Profiles and the Efficacy of EDO-S101, a First-in-Class Alkylating Histone Deacetylase Inhibition (HDACi) Fusion Molecule, in Relapsed/Refractory Hematologic Malignancies. Clinical Trials Identifier: NCT02576496, Oct. 14, 2015. 5 pages.
Clinicaltrials.gov, Bendamustine, Lenalidomide (Revlimid®) and Dexamethasone (BRd) as 2nd-line Therapy for Patients With Relapsed or Refractory Multiple Myeloma (BRd). Clinical Trials Identifier: NCT01701076, Aug. 24, 2016.
Clinicaltrials.gov, Phase 1 Trial of Dasatinib and Bendamustine in Chronic Lymphocytic Leukemia. ClinicalTrials Identifier: NCT00872976, Apr. 22, 2009. 3 pages.
Clinicaltrials.gov, Study of EDO-S101, A First-in-Class Alkylating HDACi Fusion Molecule, in Relapsed/Refractory Hematologic Malignancies. ClinicalTrials.gov Identifier: NTC02576496, 4 pages, Oct. 2015.
Clinicaltrials.gov, Study of the Safety, Pharmacokinetics and Efficacy of EDO-S101, in Patients With Advanced Solid TumorsClinical Trials Identifier: NCT03345485, Dec. 24, 2020. 12 pages.

(56) References Cited

OTHER PUBLICATIONS

Connors, Hodgkin lymphoma: special challenges and solutions. Hematol Oncol. Jun. 2015;33 Suppl 1:21-4.
Cooke et al., Spontaneous onset and transplant models of the Vk*MYC mouse show immunological sequelae comparable to human multiple myeloma. J Transl Med. Sep. 6, 2016;14:259. 12 pages.
Corazzelli et al., Efficacy and safety of bendamustine for the treatment of patients with recurring Hodgkin lymphoma. Br J Haematol. Jan. 2013;160(2):207-15.
Curigliano et al., Cardiovascular toxicity induced by chemotherapy, targeted agents and radiotherapy: ESMO Clinical Practice Guidelines. Annals of Oncology. Oct. 2012;23(Suppl. 7):vii155-vii166.
De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Blood. 2015;126(23):2479. 7 pages.
De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Istituto Nazionale Tumor, IRCCS-Fondazione Pascale, Dec. 6, 2015. 1 page.
De Filippi et al., Edo-S101, a Bendamustine (BDM)/Histone-Deacetylase Inhibitor (HDACi) Fusion Molecule, Demonstrates Potent Preclinical Activity Against T-Cell Malignancies and Overcomes BDM-Resistance. ASH, 59th Annual Meeting & Exposition. Dec. 9-12, 2017. Poster 2547. 1 page.
De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. ASH 57th Annual Meeting & Exposition. Abstract No. 2481. Dec. 5-8, 2015 [Downloaded from: [ttps://ash.confex.com/ash/2015/webprogram/Paper84797.html]. 2 pages.
De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones. Blood. 2015;126:2481, 5 pages.
DeAngelo et al., Phase 1 clinical results with tandutinib (MLN518), a novel FLT3 antagonist, in patients with acute myelogenous leukemia or high-risk myelodysplastic syndrome: safety, pharmacokinetics, and pharmacodynamics. Blood. Dec. 1, 2006;108(12):3674-81.
DeSouza et al., Has the survival of patients with glioblastoma changed over the years? Br J Cancer. Jan. 19, 2016;114(2):146-50.
Detich et al., Valproate induces replication-independent active DNA demethylation. J Biol Chem. Jul. 25, 2003;278(30):27586-92.
Diehl, The Evolution of Chemotherapy, Using the A-DAC Principle to Unlock New Treatment Options in Hodgkin Lymphoma. Mundipharma EDO Satellite Symposium, 10th International Symposium on Hodgkin Lymphoma, 6 pages, Oct. 23, 2016.
Dooley et al., Alkylating Histone Deacetylase Inhibitor Treatment in Animal Models of MPO-ANCA Vasculitis. Abstract TH-PO052. ASN, Kidney Week, Nov. 2, 2017, 2 pages.
Drogaris et al., Histone deacetylase inhibitors globally enhance h3/h4 tail acetylation without affecting h3 lysine 56 acetylation. Sci Rep. 2012;2:220. 12 pages.
Döhner et al., Diagnosis and management of acute myeloid leukemia in adults: recommendations from an international expert panel, on behalf of the European LeukemiaNet. Blood. Jan. 21, 2010;115(3):453-74.
Edoncology.com, The A-DAC Principle: A New Concept in Oncology Treatment. 3 pages, Sep. 2016.
EU Clinical Trials Register, EudraCT No. 2005-002051-41. 13 pages. Dec. 7, 2016.
EU Clinical Trials Register, EudraCT No. 2005-006083-57. 28 pages. Jun. 1, 2016.
Eurordis, Rare Diseases Europe, Why Research on Rare Diseases? Position Paper. Retrieved online at: www.eurordis.org. 14 pages. Oct. 2010.
Fei et al., Development of clinically relevant orthotopic xenograft mouse model of metastatic lung cancer and glioblastoma through surgical tumor tissues injection with trocar. J Exp Clin Cancer Res. Jun. 2, 20109;29:84.
Festuccia et al., Enhancement of radiosensitivity by the novel anticancer quinolone derivative vosaroxin in preclinical glioblastoma models. EJC, European Journal of Cancer. Dec. 2016;69(Suppl 1):S62. Abstract 174, Poster P145.
Festuccia et al., Targeting glioblastoma with UniPR1331, a new and stable bioavailable small molecule inhibiting Ephephrin interaction: In vitro and in vivo evidence. EJC, European Journal of Cancer. Dec. 2016;69(Suppl 1), Abstract 71, Poster P042.
Festuccia et al., The first-in-class alkylating deacetylase inhibitor molecule tinostamustine shows antitumor effects and is synergistic with radiotherapy in preclinical models of glioblastoma. J Hematol Oncol. Feb. 27, 2018;11(1):32. 19 pages.
Formenti et al., Results of a phase I-II study of adjuvant concurrent carboplatin and accelerated radiotherapy for triple negative breast cancer. Oncoimmunology. Dec. 27, 2016;6(3) :e1274479, 8 pages.
Frew et al., Enhancing the apoptotic and therapeutic effects of HDAC inhibitors. Cancer Lett. Aug. 8, 2009;280(2):125-33.
Furumai et al., Potent histone deacetylase inhibitors built from trichostatin A and cyclic tetrapeptide antibiotics including trapoxin. Proc Natl Acad Sci U S A. Jan. 2, 2001;98(1):87-92.
Gemmill et al., Synergistic growth inhibition by Iressa and Rapamycin is modulated by VHL mutations in renal cell carcinoma. Br J Cancer. Jun. 20, 2005;92(12):2266-77.
Geurink et al., Incorporation of non-natural amino acids improves cell permeability and potency of specific inhibitors of proteasome trypsin-like sites. J Med Chem. Feb. 14, 2013;56(3):1262-75.
Ghesquières et al., Clinical experience of bendamustine in relapsed or refractory Hodgkin lymphoma: a retrospective analysis of the French compassionate use program in 28 patients. Leuk Lymphoma. Nov. 2013;54(11):2399-404.
Gillis, Hdac Inhibition Appears to Sensitive Triple-Negative Breast Cancer Cells to Certain Treatments. Retrieved online at: https://www.onclive.com/conference-coverage/sabes-2012/hdac-inhibition-appears-to-sensitize-triplenegative-breast-cancer-cells-to-certain-treatment, 2 pages, (2012).
Golub et al., Molecular classification of cancer: class discovery and class prediction by gene expression monitoring. Science. Oct. 15, 1999;286(5439):531-7.
Graham et al., T-cell prolymphocytic leukemia. Proc (Bayl Univ Med Cent). Jan. 2013;26(1):19-21.
Gravina et al., The novel CXCR4 antagonist, PRX177561, reduces tumor cell proliferation and accelerates cancer stem cell differentiation in glioblastoma preclinical models. Tumor Biology. Jun. 2017;1-17.
Greaves et al., Clonal evolution in cancer. Nature. Jan. 18, 2012;481(7381):306-13.
Griffith et al., A novel anti-cancer bifunctional platinum drug candidate with dual DNA binding and histone deacetylase inhibitory activity. Chem Commu (Camb). Nov. 2009 28;(44):6735-7.
Griffith et al., Novel Platinum Pyridinehydroxamic Acid Complexes: Synthesis, Characterisation, X-ray Crystallographic Study of Nitric Oxide Related Properties. Polyhedron. 2007;26:4697-4706.
Groselj et al., Histone deacetylase inhibitors as radiosensitisers: effects on DNA damage signalling and repair. Br J Cancer. Mar. 5, 2013;108(4):748-54.
Guntner et al., Cerebrospinal fluid penetration of targeted therapeutics in pediatric brain tumor patients. Acta Neuropathol Commun. Jun. 3, 2020;8(1):78, 13 pages.
Hancock et al., HDAC inhibitor therapy in autoimmunity and transplantation. Ann Rheum Dis. Apr. 2012;71 Suppl 2:146-54.
Harrison et al., High Response Rates with the Combination of Bortezomib. Dexamethasone and the Pan-HistoneDeacetylase Inhibitor Romidepsin in Patients with Relapsed or Refractory Multiple Myeloma in a Phase 1/11 Clinical Trial. Blood. 2008;112, Abstract 3698. ASH Annual Meeting.

(56) References Cited

OTHER PUBLICATIONS

Hartmann et al., Bendamustine hydrochloride in patients with refractory soft tissue sarcoma: a noncomparative multicenter phase 2 study of the German sarcoma group (AIO-001). Cancer. Aug. 15, 2007;110(4):861-6.
Hedgethorne et al., FORETINIB, c-Met and VEGFR-2 Inhibitor Oncolytic. Drugs of the Future. 2010;35(11):893-902.
Hegi et al., MGMT gene silencing and benefit from temozolomide in glioblastoma. N Engl J Med. Mar. 10, 2005;352(10):997-1003.
Her et al., Targeting DNA Double-strand Break Repair in Cancer Therapy. Journal of Molecular and Genetic Medicine. Dec. 31, 2015;9:e106, 1 page.
Herbaux et al., Bendamustine is effective in T-cell prolymphocytic leukaemia. Br J Haematol. Mar. 2015;168(6):916-9.
Herold et al., Bendamustine, vincristine and prednisone (BOP) versus cyclophosphamide, vincristine and prednisone (COP) in advanced indolent non-Hodgkin's lymphoma and mantle cell lymphoma: results of a randomised phase III trial (OSHO# 19). J Cancer Res Clin Oncol. Feb. 2006;132(2):105-12.
Herold et al., BOP versus COP in Advanced Low Grade Non-Hodgkin's Lymphomas - Results of a Randomized Multicenter Study. Blood. 1999;94:262b. Abstract 4382.
Hideshima et al., Mechanism of action of proteasome inhibitors and deacetylase inhibitors and the biological basis of synergy in multiple myeloma. Mol Cancer Ther. Nov. 2011;10(11):2034-42.
Hoffman, Brentuximab Vedotin Plus Bendamustine Active In Heavily Pretreated Hodgkin Lymphoma, ALCL. Cancer Therapy Advisor, Dec. 7, 2015. 2 pages. retreived online at: http://www.cancertherapyadvisor.com/ash-2015/hodgkin-lymphoma-alcl-brentuximab-vedotin-better-treatment-risk/article/458249/.
Hong et al., Complete Durable Response From Carboplatin and Olaparib in a Heavily Pretreated Triple-Negative Metastatic Breast Cancer With Germline BRCA2 and "BRCAness" Mutations. J Oncol Pract. Mar. 2016;12(3):270-2.
Howlader et al., Contributions of Subtypes of Non-Hodgkin Lymphoma to Mortality Trends. Cancer Epidemiol Biomarkers Prev. Jan. 2016;25(1):174-9.
Hummel et al., A pediatric phase 1 trial of vorinostat and temozolomide in relapsed or refractory primary brain or spinal cord tumors: a Children's Oncology Group phase 1 consortium study. Pediatr Blood Cancer. Sep. 2013;60(9):1452-7.
Ihle et al., HR23b expression is a potential predictive biomarker for HDAC inhibitor treatment in mesenchymal tumours and is associated with response to vorinostat. The Journal of Pathology: Clinical Research. 2016;2:59-71.
Jagannath et al., Bortezomib in combination with dexamethasone for the treatment of patients with relapsed and/or refractory multiple myeloma with less than optimal response to bortezomib alone. Haematologica. Jul. 2006;91(7):929-34.
Jawhari et al., In Vitro and In Vivo Preclinical Activity of EDO-S101 in Hodgkin Lymphoma. Haematologica. 2016;101(s5):6-7, Abstract P037.
Jennette et al., Pathogenesis of antineutrophil cytoplasmic autoantibody-mediated disease. Nat Rev Rheumatol. Aug. 2014;10(8):463-73.
Jiang et al., A mammalian functional-genetic approach to characterizing cancer therapeutics. Nature Chemical Biology. Feb. 2011;7:92-100.
Kaddour et al., Transmission of Induced Chromosomal Aberrations through Successive Mitotic Divisions in Human Lymphocytes after In Vitro and ?In? Vivo Radiation. Scientific Reports. Jun. 12, 2017;7:3291, 11 pages.
Kalin et al., Creating zinc monkey wrenches in the treatment of epigenetic disorders. Curr Opin Chem Biol. Jun. 2009;13(3):263-71.
Kallenberg, Pathogenesis and treatment of ANCA-associated vasculitides. Clin Exp Rheumatol. Jul.-Aug. 2015;33(4 Suppl 92):S11-4.
Kallenberg, Pathogenesis of ANCA-associated vasculitides. Ann Rheum Dis. Mar. 2011;70 Suppl 1:i59-63.
Kalsi et al., The impact of low-grade toxicity in older people with cancer undergoing chemotherapy. Br J Cancer. Dec. 9, 2014;111(12):2224-8.
Kampa-Schittenhelm et al., Quizartinib (AC220) is a potent second generation class III tyrosine kinase inhibitor that displays a distinct inhibition profile against mutant-FLT3, -PDGFRA and -KIT isoforms. Molecular Cancer. 2013;12:19, 15 pages.
Kaufman et al., Lenalidomide. Bortezomib. and Dexamethasone (RVD) in Combination with Vorinostat As Front-Line Therapy for Patients with Multiple Myeloma (MM): Results of a Phase 1 Study. Blood. 2012;120, Abstract No. 336. 2 pages. ASH Annual Meeting.
Keating et al., Bendamustine. Nat Rev Drug Discov. Jun. 2008;7(6):473-4.
Khot et al., Panobinostat in lymphoid and myeloid malignancies. Expert Opin Investig Drugs. Sep. 2013;22(9):1211-23.
Kigawa, New strategy for overcoming resistance to chemotherapy of ovarian cancer. Yonago Acta Med. Jun. 2013;56(2):43-50.
Kim et al., Histone deacetylase inhibitors: molecular mechanisms of action and clinical trials as anti-cancer drugs. Am J Transl Res. Feb. 2011;3(2):166-79.
Knauf, Bendamustine in the treatment of chronic lymphocytic leukemia. Expert Rev Anticancer Ther. Feb. 2009;9(2):165-74.
Knittel et al., Two mouse models reveal an actionable PARP1 dependence in aggressive chronic lymphocytic leukemia. Nat Commun. Jul. 28, 2017;8(1):153. 13 pages.
Kollmannsberger et al., Phase II study of bendamustine in patients with relapsed or cisplatin-refractory germ cell cancer. Anticancer Drugs. Aug. 2000;11(7):535-9.
Koster et al., Carboplatin in Combination with Bendamustine in Previously Untreated Patients with Extensive-Stage Small Cell Lung Cancer (SCLC). Clin Drug Investig. 2004;24(10):611-8.
Kotzin et al., Reversal of nzb/nzw disease with total lymphoid irradiation. J Exp Med. Aug. 1, 1979;150(2):371-8.
Kraus et al., EDO-S101, A New Alkylating Histone-Deacetylase Inhibitor (HDAC) Fusion Molecule has Superior Activity Against Myeloma and B Cell Lympoma and Strong Synergy, With Proteasome Inhibitors in vitro. ASH, 2014.
Kraus et al., EDO-S101, A New Alkylating Histone-Deacetylase Inhibitor (HDACi) Fusion Molecule, has Superior Activity Against Myeloma and B Cell Lympoma and Strong Synergy With Proteasome Inhibitors in vitro. ASH, 2014. Publication No. 2249.
Kraus et al., EDO-S101, A New Alkylating Histone-Deacetylase Inhibitor (HDACi) Fusion Molecule, Has Superior Activity Against Myeloma and B Cell Lympoma and Strong Synergy with Proteasome Inhibitors in vitro. Blood. 2014;124;2249.
Krause et al., Tyrosine kinases as targets for cancer therapy. N Engl J Med. Jul. 14, 2005;353(2):172-87.
Kumar et al., Histone deacetylase inhibitors induce cell death in supratentorial primitive neuroectodermal tumor cells. Oncol Rep. Nov. 2006;16(5):1047-52.
Lala et al., Role of nitric oxide in tumor progression: lessons from experimental tumors. Cancer Metastasis Rev. Mar. 1998;17(1):91-106.
Layman et al., Severe and prolonged lymphopenia observed in patients treated with bendamustine and erlotinib for metastatic triple negative breast cancer. Cancer Chemother Pharmacol. May 2013;71(5):1183-90.
Le Moigne et al., The p97 Inhibitor CB-5083 Is a Unique Disrupter of Protein Homeostasis in Models of Multiple Myeloma. Molecular Cancer Therapeutics. Nov. 2017;16(11):2375-2386.
Lee et al., Phase I/Ib study of olaparib and carboplatin in BRCA1 or BRCA2 mutation-associated breast or ovarian cancer with biomarker analyses. J Natl Cancer Inst. May 19, 2014;106(6):dju089. 11 pages.
Lehmann et al., Refinement of Triple-Negative Breast Cancer Molecular Subtypes: Implications for Neoadjuvant Chemotherapy Selection. PLoS One. Jun. 16, 2016;11(6):e0157368, 22 pages.
Lentzsch et al., Combination of bendamustine, lenalidomide, and dexamethasone (BLD) in patients with relapsed or refractory multiple myeloma is feasible and highly effective: results of phase 1/2 open-label, dose escalation study. Blood. May 17, 2012;119(20):4608-13.

(56) References Cited

OTHER PUBLICATIONS

Leoni et al., Bendamustine (Treanda) displays a distinct pattern of cytotoxicity and unique mechanistic features compared with other alkylating agents. Clin Cancer Res. Jan. 1, 2008;14(1):309-17.

Leoni, Bendamustine: rescue of an effective antineoplastic agent from the mid-twentieth century. Semin Hematol. Apr. 2011;48 Suppl 1:S4-11.

Leung-Hagesteijn et al., Xbp1s-negative tumor B cells and pre-plasmablasts mediate therapeutic proteasome inhibitor resistance in multiple myeloma. Cancer Cell. Sep. 9, 2013;24(3):289-304.

Li et al., Pharmacokinetics of bendamustine in the central nervous system: chemoinformatic screening followed by validation in a murine model. MedChemComm. 2012;3:1526-1530.

Liby et al., Elevated and Deregulated Expression of HDAC3 in Human Astrocytic Glial Tumours. Folia Biologica (Praha). 2006;52:21-33.

Lin et al., Anti-rheumatic activities of histone deacetylase (HDAC) inhibitors in vivo in collagen-induced arthritis in rodents. Br J Pharmacol. Apr. 2007;150(7):862-72.

Lin et al., Treatment of Brain Metastases. J Clin Oncol. Oct. 20, 2015;33(30):3475-84.

Little et al., Experimental autoimmune vasculitis: an animal model of anti-neutrophil cytoplasmic autoantibody-associated systemic vasculitis. Am J Pathol. Apr. 2009;174(4):1212-20.

Little et al., Therapeutic effect of anti-TNF-alpha antibodies in an experimental model of anti-neutrophil cytoplasm antibody-associated systemic vasculitis. J Am Soc Nephrol. Jan. 2006;17(1):160-9.

Liu et al., A DNA/HDAC dual-targeting drug CY190602 with significantly enhanced anticancer potency. EMBO Mol Med. 12 pages, Published online: Mar. 9, 2015.

Liu et al., Effects of suberoylanilide hydroxamic acid (SAHA) combined with paclitaxel (PTX) on paclitaxel-resistant ovarian cancer cells and insights into the underlying mechanisms. Cancer Cell Int. Nov. 26, 2014;14(1):112, 11 pages.

Liu, Characterization of TCL1-Tg:P53- / -Mice that Resemble Human Chronic Lymphocytic Leukemia with 17P-Deletion. UT GSBS Thesis, Graduate School of Biomedical Sciences, Digital Commons@The Texas Medical Center, May 2013. 142 pages.

Loftsson et al., Historical Perspectives: Cyclodextrins and their pharmaceutical applications. International Journal of Pharmaceutics. 2007;329:1-11.

Loibl et al., Multicenter Phase II Study with Weekly Bendamustine and Paclitaxel as First- or Later-Line Therapy in Patients with Metastatic Breast Cancer: RiTa II Trial. Breast Care (Basel). Dec. 2011;6(6):457-461.

Lombardi et al., Predictors of survival and effect of short (40 Gy) or standard-course (60 Gy) irradiation plus concomitant temozolomide in elderly patients with glioblastoma: a multicenter retrospective study of AINO (Italian Association of Neuro-Oncology). J Neurooncol. Nov. 2015;125(2):359-67.

Lopez-Iglesias et al., Preclinical anti-myeloma activity of EDO-S101, a new bendamustine-derived molecule with added HDACi activity, through potent DNA damage induction and impairment of DNA repair. J Hematol Oncol. Jun. 20, 2017;10(1):127. 14 pages.

Lopez-Iglesias et al., Preclinical anti-myeloma activity of the alkylating-HDACi Fusion Molecule EDO-S101 Through DNA-damaging and HDACi Effects. Haematologica. 2014;99(s1):354-355, Abstract P942.

Lopez-Iglesias et al., Preclinical anti-myeloma activity of the alkylating-HDACi molecule EDO-S101 through DNA-damaging and HDACi effects. EDO, http://mundipharma-edo.com. Poster Jun. 1, 2014.

Lopez-Iglesias et al., Preclinical Anti-Myeloma Activity of the Alkylating-HDACi Molecule EDO-S101 Through DNA-Damaging and HDACi Effects. EHA 2014 Poster, Jun. 12, 2014.

Lopez-Iglesias et al., Preclinical antimyeloma activity of EDO-S101 (bendamustine- vorinostat fusion molecule) through DNA-damaging and HDACi effects. 15th International Myeloma Workshop. Sep. 23-26, 2015. Rome, Italy. Clinical Lymphoma, Myeloma & Leukemia. Sep. 2015;15(3 Suppl. 3):e218, Abstract P0-238.

Lopez-Iglesias et al., The Alkylating Histone Deacetylase Inhibitor Fusion Molecule Edo-S101 Displays Full Bi-Functional Properties in Preclinical Models of Hematological Malignancies. Blood. 2014;124:2100.

Lopez-Iglesias et al., The Hybrid Molecule, Edo-S101, Impairs Double Strand Breaks Repair in Multiple Myeloma and Synergizes with Bortezomib and Dexamethasone. Blood. 2015;126(23):5354-5354.

Lucio-Eterovic et al., Differential expression of 12 histone deacetylase (HDAC) genes in astrocytomas and normal brain tissue: class II and IV are hypoexpressed in glioblastomas. BMC Cancer. Aug. 19, 2008;8:243.

Ludwig et al., Bendamustine-bortezomib-dexamethasone is an active and well-tolerated regimen in patients with relapsed or refractory multiple myeloma. Blood. Feb. 13, 2014;123(7):985-91.

Marchion et al., Development of histone deacetylase inhibitors for cancer treatment. Expert Rev Anticancer Ther. Apr. 2007;7(4):583-98.

Marks, Discovery and development of SAHA as an anticancer agent. Oncogene. Feb. 26, 2007;26(9):1351-6.

Marmion et al., Hydroxamic Acids—An Intriguing Family of Enzyme Inhibitors and Biomedical Ligands. Eur J Inorg Chem. 2004(15):3003-3016.

McInnis et al., Dysregulation of autoantigen genes in ANCA-associated vasculitis involves alternative transcripts and new protein synthesis. J Am Soc Nephrol. Feb. 2015;26(2):390-9.

Meanwell, Synopsis of some recent tactical application of bioisosteres in drug design. J Med Chem. Apr. 28, 2011;54(8):2529-91.

Medline AN—NLM24103869, Chen et al., Dexamethasone and Vorinostat Cooperatively Promote Differentiation and Apoptosis in Kasumi-1 Leukemia Cells Through Ubiquitination and Degradation of AML1-ETO. 2 pages, Sep. 2013.

Medline/NLM AN: NLM24998648, 1 page. May 2014.

Mehrling et al., Activity of the alkylating histone-deacetylase inhibition fusion molecule EDO-S-101 in preclinical models of human glioblastoma independent from MGMT expression. Journal of Clinical Oncology. May 29, 2017;33(Suppl. 15), Abstract e13031.

Mehrling et al., Is there hope to treat glioblastoma effectively? CNS Oncol. 2015;4(6):377- 9.

Mehrling et al., The Alkylating-HDAC Inhibition Fusion Principle: Taking Chemotherapy to the Next Level with the First in Class Molecule EDO-S101. Anticancer Agents Med Chem. 2016;16(1):20-8.

Mehrling, Chemotherapy is getting 'smarter'. Future Oncol. 2015;11(4):549-52.

Mehrling, First in human clinical trails to commence Q3 2015. Mundipharma EDO GmbH. Retrieved online at: http://mundipharma-edo.com. Jul. 31, 2015. 2 pages.

Mehrling, First-in-human clinical trial of its lead compound, EDO-S101. Mundipharma EDO GmbH. Retrieved online at: http://mundipharma-edo.com. May 31, 2016. 2 pages.

Mehrling, Fusion Therapy, a New Approach to Combining Treatments. Drug Discovery World. 2016;71-76.

Mehrling, Mundipharma EDO GmbH Announces FDA Investigational New Drug Approval of its First anti-Cancer Compound, EDO-S101, for the Treatment of Patients with Relapsed/Refractory Haematologic Malignancies and Solid Tumours. EDO, http://mundipharma-edo.com/2015/07/31/mundipharma-edo-gmbh-announces-fda-investigational-new-drug-approval-of-its-first-anti-cancer-compound-edo-s101-for-the-treatment-of-patients-with-relapsedrefractory-haematologic-malignancies-and-s/. 2 pages, Jul. 31, 2015.

Mehrling, Mundipharma EDO GmbH announces first-in-human clinical trial of its lead compound, EDO-S101. EDO, http://mundipharma-edo.com/2016/07/20/mundipharma-edo-gmbh-announces-first-in-human-clinical-trial-of-lead-compound-edo-s101/. 2 pages, May 31, 2016.

Mey et al., Bendamustine, lenalidomide and dexamethasone (BRd) has high activity as 2(nd)-line therapy for relapsed and refractory multiple myeloma—a phase II trial. Br J Haematol. Mar. 2017;176(5):770-782.

Miller et al., Histone deacetylase inhibitors. J Med Chem. Nov. 20, 2003;46(24):5097-116.

(56) References Cited

OTHER PUBLICATIONS

Min et al., Histone deacetylase inhibitor, suberoylanilide hydroxamic acid (SAHA), enhances anti-tumor effects of the poly (ADP-ribose) polymerase (PARP) inhibitor olaparib in triple- negative breast cancer cells. Breast Cancer Res. Mar. 7, 2015;17:33, 13 pages.
Minucci et al., Histone deacetylase inhibitors and the promise of epigenetic (and more) treatments for cancer. Nat Rev Cancer. Jan. 2006;6(1):38-51.
Mishra et al., Histone deacetylase inhibitors modulate renal disease in the MRL-lpr/lpr mouse. J Clin Invest. Feb. 2003;111(4):539-52.
Moosman et al., Weekly treatment with a combination of bortezomib and bendamustine in relapsed or refractory indolent non-Hodgkin lymphoma. Leuk Lymphoma. Jan. 2010;51(1):149-52.
Moradei et al., Histone deacetylase inhibitors: latest developments, trends and prospects. Curr Med Chem Anticancer Agents. Sep. 2005;5(5):529-60.
Moreau et al., Phase 1b Dose Escalation Study of Oral Quisinostat, a Histone Deacetylase Inhibitor (HDACi), In Combination With Velcade (Bortezomib) and Dexamethasone for Patients With Relapsed Multiple Myeloma (MM). Blood. Nov. 15, 2013;122(21):1932.
Moreau et al., Proteasome inhibitors in multiple myeloma: 10 years later. Blood. Aug. 2, 2012;120(5):947-59.
Moscovitch et al., Successful treatment of autoimmune manifestations in MRL/l and MRL/n mice using total lymphoid irradiation (TLI). Exp Mol Pathol. Feb. 1983;38(1):33-47.
Moskowitz et al., Phase II study of bendamustine in relapsed and refractory Hodgkin lymphoma. J Clin Oncol. Feb. 1, 2013;31(4):456-60.
Moskowitz, Bendamustine: a bridge to longer term solutions in heavily treated Hodgkin lymphoma. Leuk Lymphoma. Nov. 2013;54(11):2339-40.
MRF, Melanoma Research Foundation, Melanoma Central Nervous System Metastases, Current Approaches, Challenges and Opportunities. 5 pages (2015).
Munakata et al., The discovery and the development of bendamustine for the treatment of non-Hodgkin lymphoma. Expert Opin Drug Discov. Nov. 2016;11(11):1123-1130.
Munker et al., Activity of Tyrosine Kinase Inhibitors in Multiple Myeloma. Blood. 2007;110(11):274B, Abstract 4804.
National Institute of Health, Cancer. MedlinePlus. Retrieved online at: http://www.nlm.nih.gov/medlineplus/cancer.html. 10 pages. Apr. 16, 2007.
O'Donnell et al., Cancer pharmacoethnicity: ethnic differences in susceptibility to the effects of chemotherapy. Clin Cancer Res. Aug. 1, 2009;15(15):4806-14.
O'Reilly et al., Urinary Soluble CD163 in Active Renal Vasculitis. J Am Soc Nephrol. Sep. 2016;27(9):2906-16.
Ocio et al., Deacetylase Inhibition in Haematological Malignancies—Advanced T-cell Lymphoma, Hodgkin's Lymphoma, Multiple Myeloma, Acute Myelogenous Leukaemia and Myelodysplastic Syndrome. European Haematology. 2010;4:47-50.
Ocio et al., In vitro and in vivo rationale for the triple combination of panobinostat (LBH589) and dexamethasone with either bortezomib or lenalidomide in multiple myeloma. Haematologica. May 2010;95(5):794-803.
Ocio et al., Phase I study of plitidepsin in combination with bortezomib and dexamethasone in patients with relapsed and/or refractory multiple myeloma. Journal of Clinical Oncology. 2016;34:Abstract 8006, 1 page.
Ocio et al., Triple Combinations of the HDAC Inhibitor Panobinostat (LBH589) Plus Dexamethasone with Either Lenalidomide or Bortezomib are Highly Effective in a Multiple Myeloma Mouse Model. Blood. 2007;110:Abstract 1514. ASH Annual Meeting.
Ocio, Epigenetic regulation and HAC inhibitors, Still a role for these agents in MM? Institute of Biomedical Research of Salamanca, University of Salamanca, Cancer Research Center, Slideshow. 32 pages, (2016).
Offidani et al., Efficacy and tolerability of bendamustine, bortezomib and dexamethasone in patients with relapsed-refractory multiple myeloma: a phase II study. Blood Cancer J. Nov. 22, 2013;3:e162.
Ogura et al., A multicentre phase II study of vorinostat in patients with relapsed or refractory indolent B-cell non-Hodgkin lymphoma and mantle cell lymphoma. Br J Haematol. Jun. 2014;165(6):768-76.
Oi et al., Synergistic induction of NY-ESO-1 antigen expression by a novel histone deacetylase inhibitor, valproic acid, with 5-aza-2'-deoxycytidine in glioma cells. J Neurooncol. Mar. 2009;92(1):15-22.
Oken et al., Toxicity and response criteria of the Eastern Cooperative Oncology Group. Am J Clin Oncol. Dec. 1982;5(6):649-55.
Oriol et al., Outcome after relapse of acute lymphoblastic leukemia in adult patients included in four consecutive risk-adapted trials by the PETHEMA Study Group. Haematologica. Apr. 2010;95(4):589-596.
Palmer et al., Combination Cancer Therapy Can Confer Benefit via Patient-to-Patient Variability without Drug Additivity or Synergy. Cell. Dec. 14, 2017;171(7):1678-1691.
Paris et al., Histone deacetylase inhibitors: from bench to clinic. J Med Chem. Mar. 27, 2008;51(6):1505-29.
Phan et al., An update on ethnic differences in drug metabolism and toxicity from anti- cancer drugs. Expert Opin Drug Metab Toxicol. Nov. 2011;7(11):1395-410.
Phiel et al., Histone deacetylase is a direct target of valproic acid, a potent anticonvulsant, mood stabilizer, and teratogen. J Biol Chem. Sep. 28, 2001;276(39):36734-41.
Pitha et al., Parenteral hydroxypropyl cyclodextrins: intravenous and intracerebral administration of lipophiles. J Pharm Sci. Jun. 1994;83(6):833-7.
Poenisch et al., Bendamustine/Prednisone Versus Melphalane/Prednisone in the Primary Treatment of Multiple Myeloma: an Updated Analysis of the 94BP01 Protocol. Blood. 2000;96(Suppl 1:759a), Abstract 3284, Poster Board Session 748-111.
Puetzer et al., Towards novel strategies of targeting specific vulnerabilities of T-PLL cells. AACR Annual Meeting. Jul. 2017;77(Suppl 13), Abstract 1372.
Pönisch et al., Combined bendamustine, prednisone and bortezomib (BPV) in patients with relapsed or refractory multiple myeloma. J Cancer Res Clin Oncol. Mar. 2013;139(3):499-508.
Pönisch et al., Treatment of bendamustine and prednisone in patients with newly diagnosed multiple myeloma results in superior complete response rate, prolonged time to treatment failure and improved quality of life compared to treatment with melphalan and prednisone—a randomized phase III study of the East German Study Group of Hematology and Oncology (OSHO). J Cancer Res Clin Oncol. Apr. 2006;132(4):205-12.
Qian et al., Activity of PXD101, a histone deacetylase inhibitor, in preclinical ovarian cancer studies. Mol Cancer Ther. Aug. 2006;5(8):2086-95.
Rajewski et al., Preliminary safety evaluation of parenterally administered sulfoalkyl ether beta-cyclodextrin derivatives. J Pharm Sci. Aug. 1995;84(8):927-32.
Rang et al., Glucocorticoids. Rang and Dale's Pharmacology, Sixth Edition. Elsevier, Limited, 3 pages, (2007).
Rang et al., Rang and Dale's Pharmacology, Sixth Edition. Churchill Livingstone Elsevier. Chapter 51, p. 729, (2007).
Rasheed et al., Histone deacetylase inhibitors in cancer therapy. Expert Opin Investig Drugs. May 2007;16(5):659-78.
Rasschaert et al., A phase I study of bendamustine hydrochloride administered day 1+2 every 3 weeks in patients with solid tumours. Br J Cancer. Jun. 4, 2007;96(11): 1692-8.
Rasschaert et al., A phase I study of bendamustine hydrochloride administered once every 3 weeks in patients with solid tumors. Anticancer Drugs. Jun. 2007;18(5):587-95.
Reagan-Shaw et al., Dose translation from animal to human studies revisited. FASEB J. Mar. 2008;22(3):659-61.
Regna et al., HDAC expression and activity is upregulated in diseased lupus-prone mice. Int Immunopharmacol. Dec. 2015;29(2):494-503.
Reilly et al., Modulation of renal disease in MRL/lpr mice by suberoylanilide hydroxamic acid. J Immunol. Sep. 15, 2004;173(6):4171-8.
Rengstl et al., Small and big Hodgkin-Reed-Sternberg cells of Hodgkin lymphoma cell lines L-428 and L-1236 lack consistent

(56) References Cited

OTHER PUBLICATIONS differences in gene expression profiles and are capable to reconstitute each other. PLoS One. May 15, 2017;12(5):e0177378.
Richardson et al., PANORAMA 2: panobinostat in combination with bortezomib and Dexamethasone in patients with relapsed and bortezomib-refractory myeloma. Blood. Oct. 3, 2013;122(14):2331-7.
Rodriguez-Tenreiro Y Sanchez, Hydrogels of Cyclodextrin Co-crosslinked and Interpenetrated for Controlled Drug Release. University of Santiago de Compostela, School of Pharmacy. pp. 29-32, (2006).
Ryu et al., Valproic acid downregulates the expression of MGMT and sensitizes temozolomide-resistant glioma cells. J Biomed Biotechnol. 2012;2012:987495. 9 pages.
Sampson et al., Vorinostat Enhances Cytotoxicity of SN-38 and Temozolomide in Ewing Sarcoma Cells and Activates STAT3/AKT/MAPK Pathways. PLoS One. Nov. 16, 2015;10(11):e0142704, 19 pages.
Sanchez et al., Anti-Myeloma Effects of Carfilzomib with Cyclophosphamide (CY) or Bendamustine (Ben). Blood. 2012;120(21), Abstract 2952. 54th ASH Annual Meeting adn Exposition.
Santacruz et al., The prognostic impact of minimal residual disease in patients with chronic lymphocytic leukemia requiring first-line therapy. Haematologica. May 2014;99(5):873-80.
Sarkaria et al., Mechanisms of chemoresistance to alkylating agents in malignant glioma. Clin Cancer Res. May 15, 2008;14(10):2900-8.
Saulnier et al., An Efficient Method for the Synthesis of Guanidino Prodrugs. Bioorganic & Medicinal Chemistry Letters. 1994;4(16):1985-1990.
Sawas et al., The Combination of Brentuximab Vedotin (Bv) and Bendamustine (B) Demonstrates Marked Activity in Heavily Treated Patients with Relapsed or Refractory Hodgkin Lymphoma (HL) and Anaplastic Large T-Cell Lymphoma (ALCL): Results of an International Multi Center Phase I/II Experience. Blood. 2015;126:586.
Schöffski et al., Repeated administration of short infusions of bendamustine: a phase I study in patients with advanced progressive solid tumours. J Cancer Res Clin Oncol. Jan. 2000;126(1):41-7.
Schöffski et al., Weekly administration of bendamustine: a phase I study in patients with advanced progressive solid tumours. Ann Oncol. Jun. 2000;11(6):729-34.
Serra et al., Co-clinical trial of olaparib in breast and ovarian patient-derived tumor xenografts (PDX) enables the identification of response biomarkers. Clin Cancer Res. 2016;22(Suppl 16):Abstract B02, 4 pages.
Shah et al., Comprehensive analysis of MGMT promoter methylation: correlation with MGMT expression and clinical response in GBM. PLoS One. Jan. 7, 2011;6(1):e16146.
Shipley et al., Acute myelogenous leukemia. Exp Hematol. Jun. 2009;37(6):649-58.
Siegel et al., Vorinostat in combination with lenalidomide and dexamethasone in patients with relapsed or refractory multiple myeloma. Blood Cancer J. Feb. 21, 2014;4(2):e182, 6 pages.
Simon, Optimal two-stage designs for phase II clinical trials. Control Clin Trials. Mar. 1989;10(1):1-10.
Song et al., Increased expression of histone deacetylase 2 is found in human gastric cancer. APMIS. 2005;113:264-8.
Stiborová et al., The synergistic effects of DNA-targeted chemotherapeutics and histone deacetylase inhibitors as therapeutic strategies for cancer treatment. Curr Med Chem. 2012;19(25):4218-38.
Storer, Design and analysis of phase I clinical trials. Biometrics. Sep. 1989;45(3):925-37.
Sturn et al., Genesis: cluster analysis of microarray data. Bioinformatics. Jan. 2002;18(1):207-8.
Tago et al., Repeated 0.5-Gy gamma irradiation attenuates autoimmune disease in MRL-lpr/lpr mice with suppression of CD3+CD4-CD8-B220+ T-cell proliferation and with up-regulation of CD4+CD25+Foxp3+ regulatory T cells. Radiat Res. Jan. 2008;169(1):59-66.
Takai et al., Human ovarian carcinoma cells: histone deacetylase inhibitors exhibit antiproliferative activity and potently induce apoptosis. Cancer. Dec. 15, 2004;101(12):2760-70.
Tesar et al., Limitations of standard immunosuppressive treatment in ANCA-associated vasculitis and lupus nephritis. Nephron Clin Pract. 2014;128(3-4):205-15.
Thurn et al., Rational therapeutic combinations with histone deacetylase inhibitors for the treatment of cancer. Future Oncol. Feb. 2011;7(2):263-83.
Topalian et al., Immune checkpoint blockade: a common denominator approach to cancer therapy. Cancer Cell. Apr. 13, 2015;27(4):450-61.
Trivedi et al., Management of Chemotherapy-Induced Peripheral Neuropathy. American Journal of Hematology / Oncology. Jan. 2015;11(1):4-10.
Tsai et al., Valproic Acid Enhanced Temozolomide-Induced Anticancer Activity in Human Glioma Through the p53-PUMA Apoptosis Pathway. Front Oncol. Oct. 1, 2021;11:722754, 13 pages.
Tseng et al., A comparison of the molecular subtypes of triple-negative breast cancer among non-Asian and Taiwanese women. Breast Cancer Res Treat. Jun. 2017;163(2):241-254.
Tutt et al., Oral poly(ADP-ribose) polymerase inhibitor olaparib in patients with BRCA1 or BRCA2 mutations and advanced breast cancer: a proof-of-concept trial. Lancet. Jul. 24, 2010;376(9737):235-44.
Valdez et al., Synergistic cytotoxicity of the DNA alkylating agent busulfan, nucleoside analogs and suberoylanilide hydroxamic acid in lymphoma cell lines. Leuk Lymphoma. May 2012;53(5):973-81.
Van Krieken, New developments in the pathology of malignant lymphoma. A review of the literature published from Jan.-Apr. 2016. J Hematop. Jun. 13, 2016;9(2):73-83.
Viel et al., Optimizing glioblastoma temozolomide chemotherapy employing lentiviral-based anti-MGMT shRNA technology. Mol Ther. Mar. 2013;21(3):570-9.
Vippagunta et al., Crystalline Solids. Advanced Drug Delivery Reviews. 2001;48:3-26.
Vlachostergios et al., Bortezomib downregulates MGMT expression in T98G glioblastoma cells. Cell Mol Neurobiol. Apr. 2013;33(3):313-8.
Vlachostergios et al., Bortezomib overcomes MGMT-related resistance of glioblastoma cell lines to temozolomide in a schedule-dependent manner. Invest New Drugs. Oct. 2013;31(5):1169-81.
Von Tresckow et al., An update on emerging drugs for Hodgkin lymphoma. Expert Opin Emerg Drugs. Jun. 2014;19(2):215-24.
Vyas et al., Cyclodextrin based novel drug delivery systems. J Incl Phenom Macrocycl Chem. 2008;62:23-42.
Wang et al., Effect of histone deacetylase inhibitor NL101 on rat neurons. Zhejiang Da Xue Bao Yi Xue Ban. May 2014;43(3):265-272.
Wang et al., Independent validation of a model using cell line chemosensitivity to predict response to therapy. J Natl Cancer Inst. Sep. 4, 2013;105(17):1284-91.
Wang et al., Phase 1 trial of linifanib (ABT-869) in patients with refractory or relapsed acute myeloid leukemia. Leuk Lymphoma. Aug. 2012;53(8):1543-51.
Wang et al., Toward selective histone deacetylase inhibitor design: homology modeling, docking studies, and molecular dynamics simulations of human class I histone deacetylases. J Med Chem. Nov. 3, 2005;48(22):6936-47.
Watanabe et al., Modulation of renal disease in MRL/lpr mice genetically deficient in the Alternative complement pathway factor B. J Immunol. Jan. 15, 2000;164(2):786-94..
Weil et al., Breast cancer metastasis to the central nervous system. Am J Pathol. Oct. 2005;167(4):913-20.
White, FDA accepts Mundipharma EDO's IND for EDO-S101. European Pharmaceutical Review. 4 pages, Aug. 3, 2015.
Wiegmans et al., Differences in Expression of Key DNA Damage Repair Genes after Epigenetic-Induced BRCAness Dictate Synthetic Lethality with PARP1 Inhibition. Mol Cancer Ther. Oct. 2015;14(10):2321-31.
Wikipedia, Triple-negative breast cancer. Retrieved online at: https://en.wikipedia.org/wiki/Triple-negative_breast_cancer. 7 pages, Feb. 20, 2017.

(56) References Cited

OTHER PUBLICATIONS

Wilson et al., Histone deacetylase 3 (HDAC3) and other class I HDACs regulate colon cell maturation and p21 expression and are deregulated in human colon cancer. J Biol Chem. May 12, 2006;281(19):13548-58.

Wilson et al., Relationship of p53, bcl-2, and tumor proliferation to clinical drug resistance in non-Hodgkin's lymphomas. Blood. Jan. 15, 1997;89(2):601-9.

Witzel et al., Long-term tumor remission under trastuzumab treatment for HER2 positive metastatic breast cancer—results from the HER-OS patient registry. BMC Cancer. Nov. 4, 2014;14:806. 7 pages.

Xiao et al., Antineutrophil cytoplasmic autoantibodies specific for myeloperoxidase cause glomerulonephritis and vasculitis in mice. J Clin Invest. Oct. 2002;110(7):955-63.

Xie et al., Quantitative structure-activity relationship study of histone deacetylase inhibitors. Curr Med Chem Anticancer Agents. May 2004;4(3):273-99.

Yan et al., Synergistic Inhibition of Tumor Growth and Overcoming Chemo-Resistance by Simultaneously Targeting Key Components in DNA Damage/Repair, Epigenetic, and Putative Cancer Stem Cell Signaling Pathways Using Novel Dual-Functional DNA-Alkylating/ HDAC Inhibitor and Tumor Suppressor Gene Nanoparticles in Cancer Research. Cancer Research. Apr. 15, 2012;72(8, Suppl. 1) Proceedings: AACR 103rd Annual Meeting. Abstract 2741. 2 pages.

Yardley, Drug resistance and the role of combination chemotherapy in improving patient outcomes. Int J Breast Cancer. 2013;2013:137414. 15 pages.

Zaja et al., Bendamustine salvage therapy for T cell neoplasms. Ann Hematol. Sep. 2013;92(9):1249-54.

Zhang et al., A novel suberoylanilide hydroxamic acid histone deacetylase inhibitor derivative, N25, exhibiting improved antitumor activity in both human U251 and H460 cells. Asian Pac J Cancer Prev. 2014;15(10):4331-8.

Zhao et al., Comparison of methods for evaluating drug-drug interaction. Front Biosci (Elite Ed). Jan. 1, 2010;2:241-9.

Zhu et al., Histone deacetylase 3 implicated in the pathogenesis of children glioma by promoting glioma cell proliferation and migration. Brain Res. Jul. 3, 2013;1520:15-22.

Zinzani et al., Brentuximab Vedotin in Transplant-Naïve Relapsed/ Refractory Hodgkin Lymphoma: Experience in 30 Patients. Oncologist. Dec. 2015;20(12):1413-6.

Zinzani et al., Dose Escalation of Tinostamustine in Patients with Relapsed/Refractory (R/R) Lymphoid Malignancies. Retrieved online at: https://library.ehaweb.org/eha/2019/24th/266100/delphine.remmy. dose.escalation.of.tinosta mustine.in.patients.with.relapsed.html?f= listing=3*browseby=8*sortby=1*media=1. 1 page, poster presentation. Jun. 1, 2019.

Zulkowski et al., Regression of brain metastases from breast carcinoma after chemotherapy with bendamustine. J Cancer Res Clin Oncol. Feb. 2002; 128(2):111-3.

U.S. Appl. No. 17/212,765, filed Mar. 25, 2021, 2021-0346351, Published.

U.S. Appl. No. 16/994,154, filed Aug. 14, 2020, 2021-0059989, Allowed.

U.S. Appl. No. 17/679,308, filed Feb. 24, 2022, 2022-0280485, Published.

U.S. Appl. No. 16/621,885, filed Dec. 12, 2019, 2020-0113870, Allowed.

U.S. Appl. No. 16/621,893, filed Dec. 12, 2019, 2020-0261423, Published.

U.S. Appl. No. 17/885,696, filed Aug. 11, 2022, Pending.

U.S. Appl. No. 17/730,276, filed Apr. 27, 2022, Pending.

U.S. Appl. No. 17/414,797, filed Jun. 16, 2021, 2022-0016084, Published.

Lin et al., The antiproliferative effect of C2-ceramide on lung cancer cells through apoptosis by inhibiting Akt and Nf? B. Cancer Cell Int. Jan. 6, 2014;14(1):1, 7 pages.

Cavo et al., Prognostic variables and clinical staging in multiple myeloma. Blood. Oct. 1989;74(5):1774-80.

Clinicaltrials.gov, NCT02576496, Study of Tinostamustine, First-in-Class Alkylating HDACi Fusion Molecule, in Relapsed/ Refractory Hematologic Malignancies. 12 pages, Sep. 21, 2023.

Conlan et al., Clinical significance of hematologic parameters in non-Hodgkin's lymphoma at diagnosis. Cancer. Mar. 1, 1991;67(5):1389-95.

Davis et al., Platelet effects on ovarian cancer. Semin Oncol. Jun. 2014;41(3):378-84.

Fan et al., Prognostic Significance of Blood Transfusion in Newly Diagnosed Multiple Myeloma Patients without Autologous Hematopoietic Stem Cell Transplantation. Biomed Res Int. 2017;2017:5462087, 6 pages.

Haymarket Media, Inc., Multiple Myeloma Treatment Regimens (Part 1 of 9). Retrieved online at: https://www.cancertherapyadvisor. com/wp-content/uploads/12/2018/12/multiplemyeloma_2017_r_ 80255.pdf. 9 pages, Oct. 2017.

Moisan et al., Enhancement of paclitaxel and carboplatin therapies by CCL2 blockade in ovarian cancers. Mol Oncol. Oct. 2014;8(7):1231-9.

Nair et al., A simple practice guide for dose conversion between animals and human. J Basic Clin Pharm. Mar. 2016;7(2):27-31.

Rajkumar et al., Multiple Myeloma: Diagnosis and Treatment. Mayo Clin Proc. Jan. 2016;91(1):101-19.

Sylman et al., A Temporal Examination of Platelet Counts as a Predictor of Prognosis in Lung, Prostate, and Colon Cancer Patients. Sci Rep. Apr. 26, 2018;8(1):6564, 11 pages,.

U.S. Appl. No. 13/143,155, filed Jul. 1, 2011, U.S. Pat. No. 8,609,864, Issued.

U.S. Appl. No. 14/075,145, filed Nov. 8, 2013, U.S. Pat. No. 9,096,627, Issued.

U.S. Appl. No. 14/972,750, filed Dec. 17, 2015, U.S. Pat. No. RE46,144, Issued.

U.S. Appl. No. 14/345,562, filed Nov. 3, 2014, U.S. Pat. No. 9,376,395, Issued.

U.S. Appl. No. 14/374,995, filed Jul. 28, 2014, U.S. Pat. No. 10,118,901, Issued.

U.S. Appl. No. 15/290,546, filed Oct. 11, 2016, 2018-0098969, Abandoned.

U.S. Appl. No. 15/314,162, filed Nov. 28, 2016, 2017-0151218, Abandoned.

U.S. Appl. No. 15/985,097, filed May 21, 2018, U.S. Pat. No. 10,406,138, Issued.

U.S. Appl. No. 16/517,936, filed Jul. 22, 2016, 2019-034807, Abandoned.

U.S. Appl. No. 14/212,765, filed Mar. 25, 2021, U.S. Pat. No. 11,559,516, Issued.

U.S. Appl. No. 18/086,958, filed Dec. 22, 2022, U.S. Pat. No. 12,048,688, Issued.

U.S. Appl. No. 18/743,233, filed Jun. 14, 2024, Pending.

U.S. Appl. No. 15/314,167, filed Nov. 28, 2016, U.S. Pat. No. 9,993,482, Abandoned.

U.S. Appl. No. 18/654,296, filed May 3, 2024, Pending.

U.S. Appl. No. 15/314,172, filed Nov. 28, 2016, U.S. Pat. No. 11,419,853, Issued.

U.S. Appl. No. 17/874,621, filed Jul. 27, 2022, 2023-0049350, Published.

U.S. Appl. No. 15/314,180, filed Nov. 28, 2016, U.S. Pat. No. 10,744,120, Issued.

U.S. Appl. No. 16/983,458, filed Aug. 3, 2020, Abandoned.

U.S. Appl. No. 16/994,154, filed Aug. 14, 2020, U.S. Pat. No. 11,541,038, Issued.

U.S. Appl. No. 18/083,651, filed Dec. 19, 2022, U.S. Pat. No. 12,064,417, Issued.

U.S. Appl. No. 18/775,245, filed Jul. 17, 2024, Pending.

U.S. Appl. No. 16/341,089, filed Apr. 11, 2019, U.S. Pat. No. 11,266,631, Issued.

U.S. Appl. No. 17/679,308, filed Feb. 24, 2022, U.S. Pat. No. 11,766,424, Issued.

U.S. Appl. No. 18/446,522, filed Aug. 9, 2023, 2024-0082220, Published.

U.S. Appl. No. 16/621,885, filed Dec. 12, 2019, U.S. Pat. No. 11,559,516, Issued.

(56) References Cited

OTHER PUBLICATIONS

U.S. Appl. No. 18/108,736, filed Feb. 13, 2023, 2023-0277507, Published.
U.S. Appl. No. 16/621,893, filed Dec. 12, 2019, U.S. Pat. No. 11,896,583, Issued.
U.S. Appl. No. 18/404,810, filed Jan. 4, 2024, 2024-0261265, Published.
U.S. Appl. No. 16/621,896, filed Dec. 12, 2019, U.S. Pat. No. 11,413,276, Issued.
U.S. Appl. No. 17/885,696, filed Aug. 11, 2022, U.S. Pat. No. 11,786,509, Issued.
U.S. Appl. No. 18/244,913, filed Sep. 12, 2023, 2024-0139155, Published.
U.S. Appl. No. 16/621,898, filed Dec. 12, 2019, U.S. Pat. No. 11,318,117, Issued.
U.S. Appl. No. 17/730,276, filed Apr. 27, 2022, U.S. Pat. No. 11,918,558, Issued.
U.S. Appl. No. 18/422,118, filed Jan. 25, 2024, 2024-0316009, Published.
U.S. Appl. No. 14/414,797, filed Jun. 16, 2021, 2022-0016084, Published.
U.S. Appl. No. 17/414,806, filed Jun. 16, 2021, 2022-0016085, Published.
U.S. Appl. No. 18/420,883, filed Jan. 24, 2024, 2024-0252472, Published.

\* cited by examiner

COMPOUNDS FOR TREATING BRAIN CANCER

CROSS-REFERENCE TO RELATED APPLICATIONS

This application is a continuation application of U.S. application Ser. No. 15/314,172, filed on Nov. 28, 2016, which is a U.S. national stage filing under 35 U.S.C. § 371(c) of International Application No. PCT/EP2015/056667, filed on Mar. 26, 2015, which claims foreign priority of U.K. Patent Application No. 1409471.8, filed on May 28, 2014. The entire contents of each of the aforementioned applications are incorporated herein by reference.

FIELD OF THE INVENTION

The present invention relates to novel treatments of brain cancers that have been particularly resistant to treatment in the past, namely astrocytic brain tumours, brain cancers that are metastasized cancers and primary CNS lymphomas.

BACKGROUND TO THE INVENTION

Cancer is one of the most life threatening diseases. Cancer is a condition in which cells in a part of the body experience out-of-control growth. According to latest data from American Cancer Society, it is estimated there were 1.67 million new cases of cancer in USA in 2014.

Cancer is the second leading cause of death in the United States (second only to heart disease) and it is estimated to have claimed more than 585,000 lives in 2014. In fact, it is estimated that 50% of all men and 33% of all women living in the United States will develop some type of cancer in their lifetime. Therefore cancer constitutes a major public health burden and represents a significant cost in the United States. These figures are reflected elsewhere across most countries globally, although the types of cancer and relative proportions of the population developing the cancers vary depending upon many different factors such including genetics and diet.

The World Health Organisation (WHO) classifies the primary brain tumours in four categories. WHO grade I and II are low-grade gliomas, whereas anaplastic astrocytomas and anaplastic oligodendrogliomas (WHO grade III), as well as glioblastomas (GBMs) (WHO grade IV), are collectively referred to as malignant gliomas. The prognosis of most primary and secondary brain tumours is abysmal due to lack of effective therapeutic agents. They are the leading cause of death from solid tumours in children and the third leading cause of death from cancer in adolescents and adults aged 15-34 years (Jemal et al, CA Cancer J Clin 59 2009 225-249).

Among the malignant gliomas, GBMs are the most common and fatal neoplasms, representing approximately 50% of all gliomas. GBM has a dismal prognosis, highlighting the need for novel treatment strategies. Surgery followed by a combined therapy of the alkylating agent temozolomide (TMZ) and radiotherapy is the standard treatment for patients suffering from GBM. The principal mechanism of action of TMZ is initiated by abnormal methylations of DNA bases, particularly 06-methylguanine in DNA (Verbeek et al, Br Med Bul, 85, 2008, 17-33).

However, many patients are resistant or show only weak reaction to TMZ. This has been shown to be conferred by O6-methylguanine-DNA methyltransferase (MGMT) mediated mismatch repair (MMR) (see Weller et al, Nat Rev Neurol, 6, 2010, 39-51). Patients having this repair system have 'MGMT positive GBMs.' The activation of mTOR/DNAPKC pathways is also believed to play a part. No chemotherapeutic agents have been developed to date which are active against MGMT positive GBMs. The activity of MGMT is also important in other astrocytic brain tumours, namely diffuse astrocytomas (WHO grade II) and anaplastic astrocytomas (WHO grade III). Progression of these to GBMs is primarily mediated through methylation by MGMT. It can therefore be seen that a therapeutic agent which is active against MGMT positive astrocytomas will be desirable in preventing advance of these diffuse and anaplastic astrocytomas to GBMs.

It is therefore essential that a novel therapeutic agent with an excellent anti-neoplastic activity against not only against MGMT negative GBMs but also against MGMT positive GBMs (as well as other astrocytic brain tumours), which shows excellent CNS penetration and has a tolerable toxicity profile is urgently developed.

A metastatic brain tumour starts as a cancer elsewhere in the body and spreads to the brain. Breast, lung, melanoma, colon and kidney cancers commonly metastasize. Frequently, the metastatic brain tumour is discovered before the primary tumour. Metastatic brain tumours are the most common of all brain tumours in adults. It is estimated that there may be up to 170,000 new cases each year. Although a little better than for GBMs, the prognosis for metastatic brain cancers is generally poor. Once again, a combination of surgery, therapy and chemotherapy is adopted, with the exact combination from within these options being dependent upon the nature of the metastatic cancer and the stage of development (as well as the health of the patient). Surgery (where possible) and radiotherapy is the standard treatment applied. Chemotherapy is sometimes employed. Unfortunately, none to date have been very successful. Part of this is due to the need for the chemotherapeutic agent to show excellent CNS penetration (as well, of course, as excellent anti-neoplastic activity and a tolerable toxicity profile). Many existing chemotherapeutic agents show a poor penetration across the blood-brain barrier. There is an urgent need for a novel therapeutic agent that addresses these problems.

Primary central nervous system (CNS) lymphoma originates in the lymphocytes but should be considered a brain tumour because its location is solely in the brain and the therapeutic challenges resemble those of other brain tumours. In particular, drug delivery is impaired by the blood-brain barrier and cerebral toxicity limits the use of current treatments. Most primary CNS lymphomas are diffuse large B-cell lymphomas (about 90%). Although it is relatively rare, its incidence and prevalence are increasing. Currently, the median survival rate with existing treatment regimes is 44 months. No particularly effective treatment regimen has yet been established for this condition. The current preferred chemotherapeutic agent is methotrexate. However, its penetration across the blood-brain barrier is not satisfactory and it has to be administered in very high doses. Combination therapy with radiotherapy can improve outcomes, but side effects can be very severe. There is therefore a need for an improved chemotherapeutic agent which has a greater ability to penetrate the blood-brain barrier and also shows excellent anti-neoplastic activity against primary CNS lymphomas.

In WO-A-2010/085377, the compound of formula I below is disclosed. It is a first-in-class dual-functional alkylating-HDACi fusion molecule which potently inhibits the HDAC pathway.

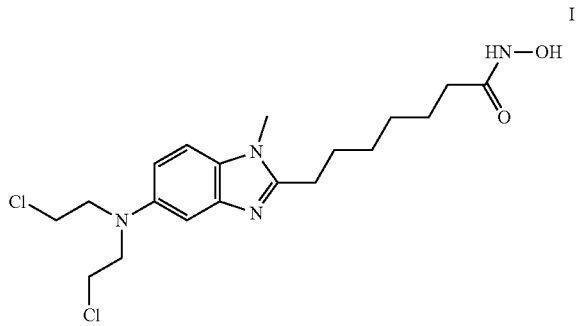 [SMILES: Cn1c(CCCCCCC(=O)NO)nc2cc(N(CCCl)CCCl)ccc21]

Biological assays showed that the compound of formula I potently inhibits class 1 and class 2 HDAC enzymes (e.g. HDAC1 $IC_{50}$ of 9 nM) and it has been shown to have excellent in vitro activity against multiple myeloma cell lines. Moreover, it suppresses DNA repair via significant downregulation of FANCD2, BRCA1, BRCA2, and TS (Thymidylate synthetase), possibly related to HDAC6 and HDAC8 inhibition. Cytotoxicity assay in NCI-60 cell lines has shown that it has a very potent anticancer activity with a median $IC_{50}$ value of 2.2 µM compared to 72 µM for Bendamustine. WO-A-2013/113838 includes data that demonstrates the activity of the compound of formula I (referred to as NL-101 in the description) against a number of cell lines, including some glioblastoma cell lines. However, each of the cell lines in question is a MGMT negative GBM tumour cell line.

SUMMARY OF THE INVENTION

In a first aspect of the present invention there is provided a compound of formula I or a pharmacologically acceptable salt thereof:

I for use in the treatment of a brain cancer selected from a MGMT positive astrocytic brain tumour, a metastatic brain cancer and primary CNS lymphoma.

In pre-clinical in vitro and in vivo studies it has been shown that the compound of formula I is active against not only MGMT negative GBM tumours but also MGMT positive GBM tumours. From this, it can also be expected that it would be active against other MGMT positive astrocytic tumours. It has also been found that the compound of formula I is able to penetrate the blood-brain barrier very well, making it ideal for therapeutic use against not only MGMT positive astrocytic tumours, but also other brain tumours. In particular, it has been further found to have very good activity against metastatic brain cancer and also primary CNS lymphoma.

In a second aspect of the present invention there is provided use of a compound of formula I or a pharmacologically acceptable salt thereof in the manufacture of a medicament for the treatment of a brain cancer selected from a MGMT positive astrocytic brain tumour, a metastatic brain cancer and primary CNS lymphoma.

In a third aspect of the present invention there is provided a method of treating a brain cancer selected from a MGMT positive astrocytic brain tumour, a metastatic brain cancer and primary CNS lymphoma in a patient in need thereof comprising administering to said patient a compound of formula I or a pharmacologically acceptable salt thereof.

DETAILED DESCRIPTION OF THE INVENTION

Figure 1:
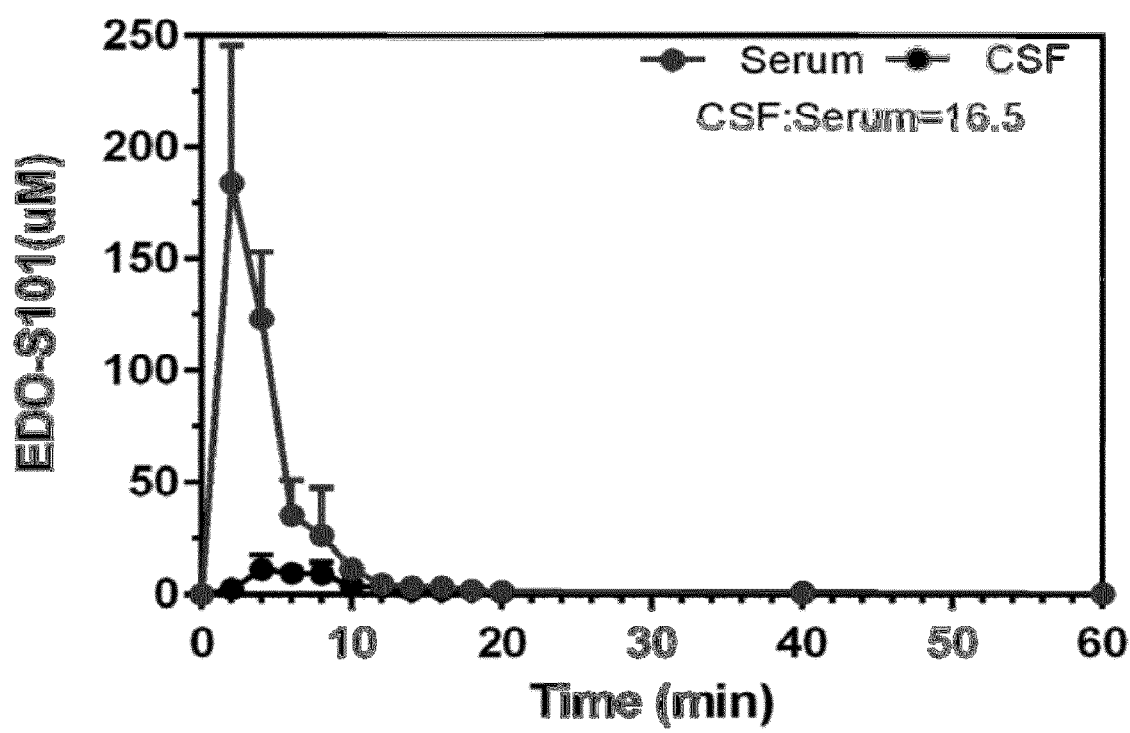
FIG. 1 is a plot of EDO-S101 concentration (µM) versus time in the cerebrospinal fluid and the blood versus time.

In the present invention, a number of general terms and phrases are used, which should be interpreted as follows.

An astrocytic brain tumour is a tumour derived from star-shaped glial cells (astrocytes) in the brain. They are divided into low grade (I and II) and high grade (III and IV). Grade II astrocytic tumours are known as diffuse astrocytomas. Although these grow relatively slowly they can develop into malignant primary tumours. Grade III astrocytic tumours are known as anaplastic astrocytomas. These are malignant tumours; they grow more rapidly and tend to invade nearby healthy tissue. Grade IV astrocytic tumours are known as glioblastoma multiforme (GBM).

These are highly malignant, growing rapidly, spreading readily to nearby tissue and are very difficult to treat with conventional treatments.

The current standard chemotherapeutic treatment is with temozolomide (TMZ). However, many patients are resistant or show only weak reaction to reaction. This has been shown to be conferred by O6-methylguanine-DNA methyltransferase (MGMT) mediated mismatch repair (MMR) (see Weller et al, Nat Rev Neurol, 6, 2010, 39-51). Patients having this repair system have 'MGMT positive GBMs.' GBMs are thus divided up as MGMT negative GBMs and MGMT positive GBMs depending upon whether they express the MGMT gene. The compounds of formula I of the present invention or a pharmacologically acceptable salt thereof have been shown to be active against not only MGMT negative GBMs but also MGMT positive GBMs.

The activity of MGMT is also important in other astrocytic brain tumours, namely diffuse astrocytomas (WHO grade II) and anaplastic astrocytomas (WHO grade III). Progression of these to GBMs is primarily mediated through methylation by MGMT. It can therefore be seen that as the compound of formula I and pharmacologically salts thereof are active against MGMT positive astrocytomas, it will also be capable of preventing advance of these diffuse and anaplastic astrocytomas to GBMs.

A metastatic brain tumour is a brain tumour that starts as a cancer elsewhere in the body and spreads to the brain. Breast, lung, melanoma, systemic lymphoma, sarcoma, colon, gastro-intestinal and kidney cancers commonly metastasize.

A primary CNS lymphoma in the context of the present invention is a lymphoma that originates in the lymphocytes in the brain, malignant cells formed from said lymphocytes. It is hence considered a brain tumour because its location and therapeutic challenges resemble those of other brain tumours.

"Pharmaceutically acceptable salts" means salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulfate, bisulfate, sulfamate, nitrate, phosphate, and organic acid addition salts such as, for example, acetate, trifluoroacetate, maleate, fumarate, citrate, oxalate, succinate, tartrate, salicylate, tosylate, lactate, naphthalenesulphonate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

In the present invention, the pharmacologically acceptable salt of the compound of formula I may preferably be the hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate or acetate, and more preferably the acetate.

In the present invention, when the compound of formula I or a pharmacologically acceptable salt thereof is for use in the treatment of a MGMT positive astrocytic brain tumour, this is preferably selected from a MGMT positive glioblastoma multiforme, a diffuse (WHO grade II) astrocytoma and an anaplastic (WHO grade III) astrocytoma, and most preferably a MGMT positive glioblastoma multiforme.

In the present invention, when the compound of formula I or a pharmacologically acceptable salt thereof is for use in the treatment of a metastatic brain cancer, this is preferably selected from metastasized breast cancer, metastasized systemic lymphoma, metastasized lung cancer, metastasized melanoma, metastasized sarcoma and metastasized gastrointestinal cancer, and most preferably metastasized breast cancer.

The therapeutically effective amount of the compound of formula I or a pharmacologically acceptable salt and the medicament comprising it administered to the patient according to the first, second and third aspects of the present invention is an amount which confers a therapeutic effect in accordance with the present invention on the treated subject, at a reasonable benefit/risk ratio applicable to any medical treatment. The therapeutic effect may be objective (i.e. measurable by some test or marker) or subjective (i.e. subject gives an indication of or feels an effect). An effective amount of the compound of formula I or a pharmacologically acceptable salt thereof according to the present invention is believed to be one wherein the compound of formula I or a pharmacologically acceptable salt thereof is included at a dosage range of from 0.1 to 70 mg/kg body weight patient (e.g. 0.5 to 50 mg/kg body weight such as 1, 5, 10, 20, 30, 40 or 50 mg/kg body weight).

The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

Suitable examples of the administration form of the compound of formula I or a pharmacologically acceptable salt thereof and medicament comprising the same according to the first, second and third aspects of the present invention include without limitation oral, topical, parenteral, sublingual, rectal, vaginal, ocular, and intranasal. Parenteral administration includes subcutaneous injections, intravenous, intramuscular, intrasternal injection or infusion techniques. Preferably, the compound of formula (I) or a pharmacologically acceptable salt thereof and medicament comprising the same are administered parenterally, and most preferably intravenously.

Preferably, the compound of formula I or a pharmacologically acceptable salt thereof is administered intravenously to the patient in need thereof at a dosage level to the patient in need thereof of from 0.1 mg/kg to 70 mg/kg body weight patient, and most preferably intravenously to the patient in need thereof at a dosage level of from 0.5 mg/kg to 50 mg/kg body weight patient.

It has been found that in the first, second and third aspects of the present invention, the compound of formula I or a pharmacologically acceptable salt thereof or medicament comprising the same may preferably be administered to a patient in need thereof on days 1, 8 and 15 of a treatment cycle, on days 1 and 8 of a treatment cycle or day 1 only of a treatment cycle.

In another preferred embodiment of the first, second and third aspects of the present invention it has surprisingly been found that the compound of formula I and pharmacologically acceptable salts thereof are considerably more effective when administered in combination with radiotherapy, and indeed appear to be synergistic with radiotherapy both in in vitro and in vivo studies. As a consequence, in the first, second and third aspects of the present invention the compound of formula I or a pharmacologically acceptable salt thereof or the medicament comprising the same may be used in treatment of a patient in need thereof wherein the patient in need thereof is also given radiotherapy either prior to or after the treatment of the brain cancer with the compound of formula I or a pharmacologically acceptable salt thereof or the medicament comprising the same. Preferably, the patient is given radiotherapy treatment prior to the treatment with the compound of formula I or a pharmacologically acceptable salt thereof or the medicament comprising the same. The radiotherapy may be given at a dose of 1 to 5 Gy over 5 consecutive days and preferably 2 Gy over 5 consecutive days.

In a further preferred embodiment of the first, second and third aspects of the present invention, the treatment further comprises the administration to a patient in need thereof of a vascular endothelial growth factor (VEGF) inhibitor, and the compound of formula I or a pharmacologically acceptable salt thereof and the vascular endothelial growth factor (VEGF) inhibitor may be administered concurrently, sequentially or separately, and preferably concurrently. Preferably, the vascular endothelial growth factor (VEGF) inhibitor is bevacizumab.

In a further preferred embodiment of the first, second and third embodiments of the present invention, the treatment further comprises the administration to a patient in need thereof of a poly ADP ribose polymerase (PARP) inhibitor, and the compound of formula I or a pharmacologically acceptable salt thereof and the poly ADP ribose polymerase (PARP) inhibitor may be administered concurrently, sequentially or separately, and preferably concurrently. Preferably, the poly ADP ribose polymerase (PARP) inhibitor is selected from rucaparib, olaparib and veliparib.

In a further preferred embodiment of the first, second and third embodiments of the present invention, the treatment further comprises the administration to a patient in need thereof of a PD-1/PDL-1 (immune checkpoint) inhibitor, and the compound of formula I or a pharmacologically acceptable salt thereof and the PD-1/PDL-1 (immune checkpoint) inhibitor may be administered concurrently, sequentially or separately, and preferably concurrently. Preferably, the PD-1/PDL-1 (immune checkpoint) inhibitor is ipilimumab.

When intended for oral administration, the compound of formula I or a pharmacologically acceptable salt thereof or medicament comprising the same of the first, second and third aspects of the present invention may be in solid or liquid form, where semi-solid, semi-liquid, suspension and gel forms are included within the forms considered herein as either solid or liquid.

The compound of formula I or a pharmacologically acceptable salt thereof or medicament comprising the same of the first, second and third aspects of the present invention can be prepared for administration using methodology well known in the pharmaceutical art. Examples of suitable pharmaceutical formulations and carriers are described in "Remington's Pharmaceutical Sciences" by E. W. Martin.

As a solid composition for oral administration, the compound of formula I or a pharmacologically acceptable salt thereof or medicament comprising the same of the first, second and third aspects of the present invention can be formulated into a powder, granule, compressed tablet, pill, capsule, chewing gum, wafer or the like form. Such a solid composition typically contains one or more inert diluents, either as a single tablet comprising all active agents or as a number of separate solid compositions, each comprising a single active agent of the combination of the present invention (in the case of the kit). In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

When the compound of formula I or a pharmacologically acceptable salt thereof or medicament comprising the same of the first, second and third aspects of the present invention is in the form of a capsule (e.g. a gelatin capsule), it can contain, in addition to materials of the above type, a liquid carrier such as polyethylene glycol, cyclodextrin or a fatty oil.

The compound of formula I or a pharmacologically acceptable salt thereof or medicament comprising the same of the first, second and third aspects of the present invention can be in the form of a liquid, e.g. an elixir, syrup, solution, emulsion or suspension. The liquid can be useful for oral administration or for delivery by injection. When intended for oral administration, a compound of formula I or a pharmacologically acceptable salt thereof or medicament comprising the same of the first, second and third aspects of the present invention can comprise one or more of a sweetening agent, preservatives, dye/colorant and flavor enhancer. In a compound of formula I or a pharmacologically acceptable salt thereof or medicament comprising the same of the first, second and third aspects of the present invention for administration by injection, one or more of a surfactant, preservative, wetting agent, dispersing agent, suspending agent, buffer, stabilizer and isotonic agent can also be included.

The preferred route of administration is parenteral administration including, but not limited to, intradermal, intramuscular, intraperitoneal, intravenous, subcutaneous, intranasal, epidural, intranasal, intracerebral, intraventricular, intrathecal, intravaginal or transdermal. The preferred mode of administration is left to the discretion of the practitioner, and will depend in part upon the site of the medical condition (such as the site of cancer). In a more preferred embodiment, the compound of formula I or a pharmacologically acceptable salt thereof or medicament comprising the same of the first, second and third aspects of the present invention are administered intravenously.

The liquid compound of formula I or a pharmacologically acceptable salt thereof or medicament comprising the same of the first, second and third aspects of the present invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides, polyethylene glycols, glycerin, or other solvents; antibacterial agents such as benzyl alcohol or methyl paraben; and agents for the adjustment of tonicity such as sodium chloride or dextrose. A parenteral combination or composition can be enclosed in an ampoule, a disposable syringe or a multiple-dose vial made of glass, plastic or other material. Physiological saline is a preferred adjuvant.

The compound of formula I or a pharmacologically acceptable salt thereof or medicament comprising the same of the first, second and third aspects of the present invention of the present invention can be administered by any convenient route, for example by infusion or bolus injection, by absorption through epithelial or mucocutaneous linings, and preferably by bolus injection.

EXAMPLES

In the following examples, the compound having the following formula I is referred to as EDO-S101.

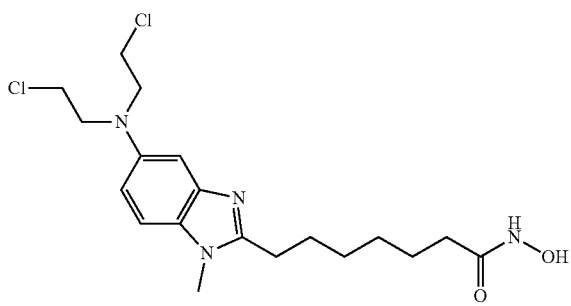

I

EDO-S101 was prepared as described in Example 6 of WO-A-2010/085377. EDO-S101 was dissolved in DMSO (100× mother solution) and stored at 4° C. before to be suspended in medium on the day of use.

Example 1 CNS Pharmacokinetic Analysis of EDO-S101 in Sprague-Dawley Rats

CNS pharmacokinetics was determined in rats after a tail vein injection of EDO-S101 at 40 mg/kg. Microdialysate samples were collected from the blood and a ventricle of the brain via microdialysis probes at 18 time intervals. The drug concentrations in these samples were determined by capillary electrophoresis with UV detection (CE-UV) followed by calculations for various pharmacokinetic parameters.

Six rats were anesthetized with gasiform isoflurane (1% isoflurane in a mixture of 20% oxygen and 80% nitrogen gas) and immobilized in a stereotaxic frame (KOPF Instruments, Tujunga, CA). Anaesthesia was maintained during the entire procedure. Each guide cannula (CMA Microdialysis Inc., Acton, MA) was stereotactically implanted into the lateral ventricle (AP −0.9, L 1.6, V 3.4, relative to bregma and skull), then secured to the skull by screws and dental cement. Following surgery, each rat was housed individually with food and water ad libitum for 3 days for recovery from cannulation surgery. Microdialysis experiments were carried out on conscious, freely moving rat. On the day of the experiment, the stylet in the guide cannula was replaced with the microdialysis probe (CMA/11 with 4 mm membrane, CMA Microdialysis Inc., Acton, MA) and a vascular microdialysis probe (CMA/20 with 4 mm membrane, CMA Microdialysis Inc, Acton, MA)) was implanted into the jugular vein. The probes had inlet tubes connected to syringes to deliver artificial cerebrospinal fluid (146 mM NaCl, 1.2 mM $CaCl_2$, 3 mM KCl, 1 mM $MgCl_2$, 1.9 mM $Na_2HPO_4$, 0.1 mM $NaH_2PO_4$, pH 7.4) into the ventricle and Dulbecco's phosphate-buffered saline (D-PBS) into the blood at 0.5 µl/min flow rate. The outlet tubes were connected to a microfraction collector for collecting the micro-dailysates at 4° C. The rats were allowed to recover for at least 24 hours prior to dosing. Eighteen samples were collected over 3 hours after EDO-S101 injection (intravenously). All samples were applied to the capillary electrophoresis with UV detection (CE-UV) for the determination of concentration of EDO-S101 in the cerebrospinal fluid (CSF) and blood. The rats were sacrificed using $CO_2$ inhalation after the experiment. The position of the probe was verified by visual inspection at the end of each experiment.

EDO-S101 in the microdialysate were measured by CE-UV (Agilent 3D CE). Briefly, the capillaries were preconditioned with 1 M sodium hydroxide for 2 min, water for 2 min and running buffer [100 mmol/l solution of ammonium acetate (adjust to pH 3.1 with acetic acid)-acetonitrile (50:50, v/v)] for 3 min. The samples were injected at a pressure of 0.7 psi for 5 s and the injection volume was approximately 5 nl. After injection, EDO-S101 was separated in a fused silica capillary of 50 µm I.D. and 50/65 cm length (effective length/total length) under 15 kv and 25° C. The absorbance from EDO-S101 was detected with UV at 300 nM. Emission was collected on a photomultiplier tube (PMT).

To perform a statistical analysis on the data, a two-way repeated measures ANOVA followed by Tukey's test was used. P<0.05 was considered significant. CNS penetration is determined as the ratio of CSF and blood area under the curve (AUC).

On analysing the results, it was found that EDO-S101 crosses the blood brain barrier well with a CNS penetration of 16.5% (see FIG. 1). It can achieve a high CNS concentration with a $C_{max}$ of 11.2 µM. As such, EDO-S101 is ideal for therapeutic use in brain tumours. It was also shown that it has a very short half-life of about 6 minutes in the blood and about 9 minutes in the brain. As the drug concentrations were determined based of the absorbance of EDO-S101 at UV wavelength of 300 nM, all the measurements are on the unmetabolized EDO-S101. The results are summarised in Table 1 as follows.

TABLE 1

| PK parameters | Blood | Brain |
|---|---|---|
| $C_{max}$ (µM) | 184.0 ± 61.8 | 11.2 ± 6.5 |
| $T_{max}$ (min) | 2.33 ± 0.82 | 5.67 ± 1.97 |
| $T_{1/2}$ (min) | 5.6 ± 1.07 | 8.8 ± 1.43 |
| AUC (0-12) (µM · hr) | 824.3 ± 110.8 | 136.2 ± 74.7 |
| AUC ratio (Brain:Blood) | 16.5% ± 0.09 | |

Example 2 In Vitro Activity Tests for EDO-S101 and Known Compounds Against Various MGMT Positive and Negative Cell Lines In vitro experiments were devised in which a series of GBM cell lines representative for MGMT negative and MGMT positive tumour cells were used.

Compounds: 1-100 µM EDO-S101, 1-50 µM temozolomide (TMZ), 1-50 µM temozolomide+500 nM vorinostat, 1-40 µM bendamustine, 1-40 µM bendamustine and 500 nM vorinostat.

Cell lines: A172, LN229, SNB19, SW1783, U251, U373 and U87: MGMT negative cell lines; LN18, Mz54, T98G, U138, U118: MGMT positive cell lines Twelve glioblastoma cell lines representing grade III and IV gliomas and with different expression of MGMT, drug and radiotherapy sensitivity and five patient derived glioblastoma stem, cells were used (see above). Four patient-derived glioblastoma stem cells, kindly provided from J. Gregory Cairncross, and Samuel Weiss at the Hotchkiss Brain Institute, Faculty of Medicine, University of Calgary, Calgary, Alberta, Canada and one luciferase transfected, PTC #8, from Prof Angelo Vescovi, University la Bicocca, Milan were cultured in defined culture serum free medium (SFM) and in non-adherent spheres culture. Cells were resuspended in DMEM/F12 media without serum supplemented with 20 ng/ml epidermal growth factor (Sigma-Aldrich), 20 ng/ml basic fibroblast growth factor (Sigma-Aldrich), B-27 supplement 1× (Gibco, Life Technologies), and antibiotics. Treatment with EDO-S101 was added straight after plating $3 \times 10^3$ cells in 96-well plates with the stem cells media. Spheres were counted 5 days after treatment under an inverted microscope at ×4 magnification. A sphere was counted if it had at least 15 cells.

Cells were seeded at a density of $2 \times 10^4$ cells/ml in 24 well plates. Cells were left to attach and grow in 5% FCS DMEM for 24 h. After this time, cells were maintained in the appropriate culture conditions. Morphological controls were performed every day with an inverted phase-contrast photomicroscope (Nikon Diaphot, Tokyo, Japan), before cell trypsinization and counting. Cells trypsinized and resuspended in 1.0 ml of saline were counted using the Nucleo-Counter™ NC-100 (automated cell counter systems, Chemotec, Cydevang, DK) in order to evaluate cell viability. All experiments were conducted in triplicate. $IC_{50}$ values were calculated by the GraFit method (Erithacus Software Limited, Staines, UK). Cell viability was measured with the 3-(4,5 dimethylthiazol-2-yl)-2,5-diphenyl tetrazolium bromide (MTT; Sigma-Aldrich) assay.

$IC_{50}$ and $IC_{20}$ values for all twelve cell lines against bendamustine and vorinostat were also determined as described above. Next, combination assays with fixed dose of vorinostat ($IC_{20}$ value) and varying the dose of bendamustine were performed. New $IC_{50}$ values were calculated for bendamustine when combined with vorinostat.

Figure 2:
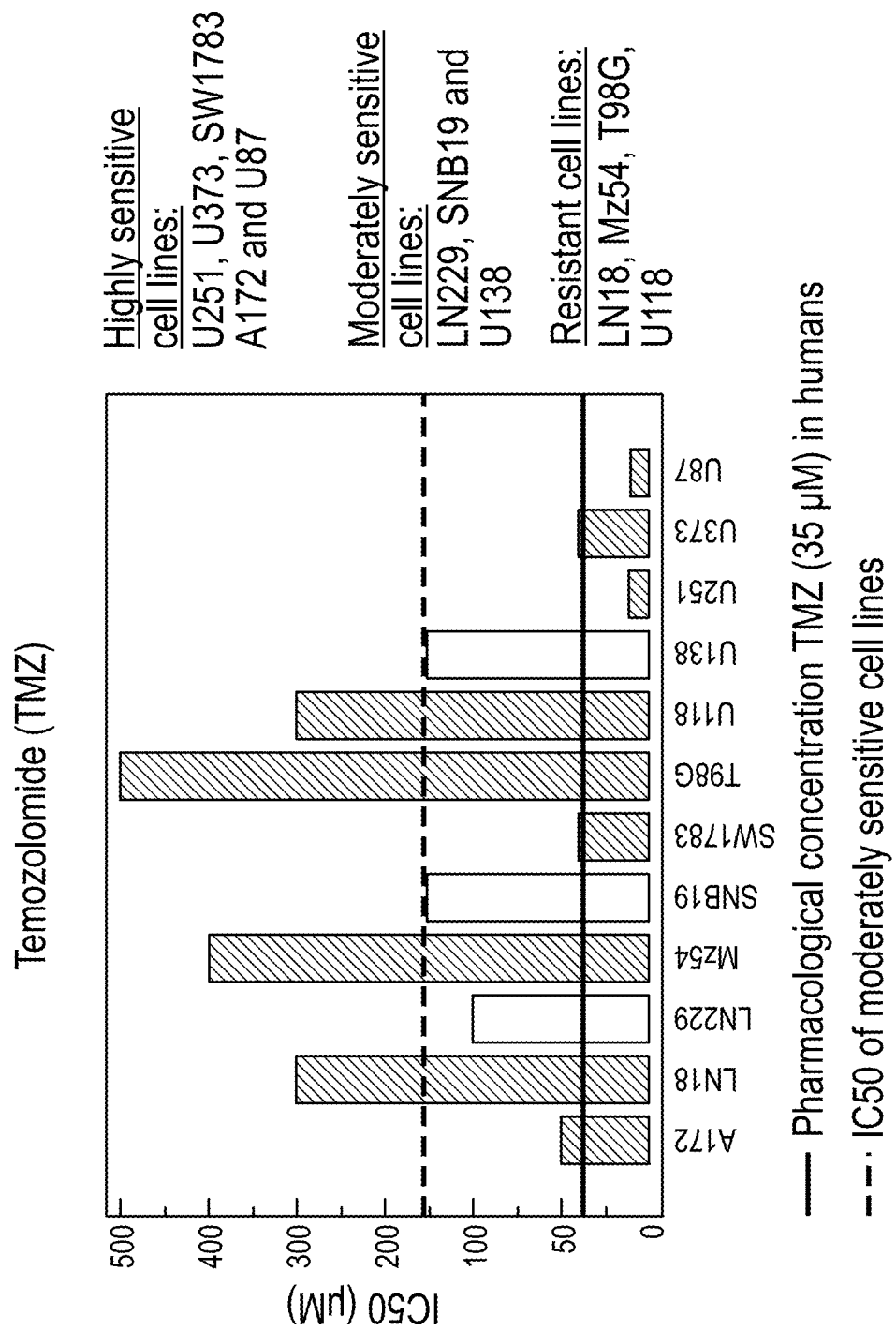
FIG. 2 is a plot of the $IC_{50}$ for the twelve tested GBM cell lines after temozolomide was administered.

As can be seen from FIG. 2, the U251, U373, SW1783, A172 and U87 GBM cell lines are highly sensitive to TMZ, while LN229, SNB19 and U138 are moderately sensitive. The MGMT positive GBM cell lines LN18, Mz54, T98G and U118 were, however, resistant to TMZ.

Figure 3:
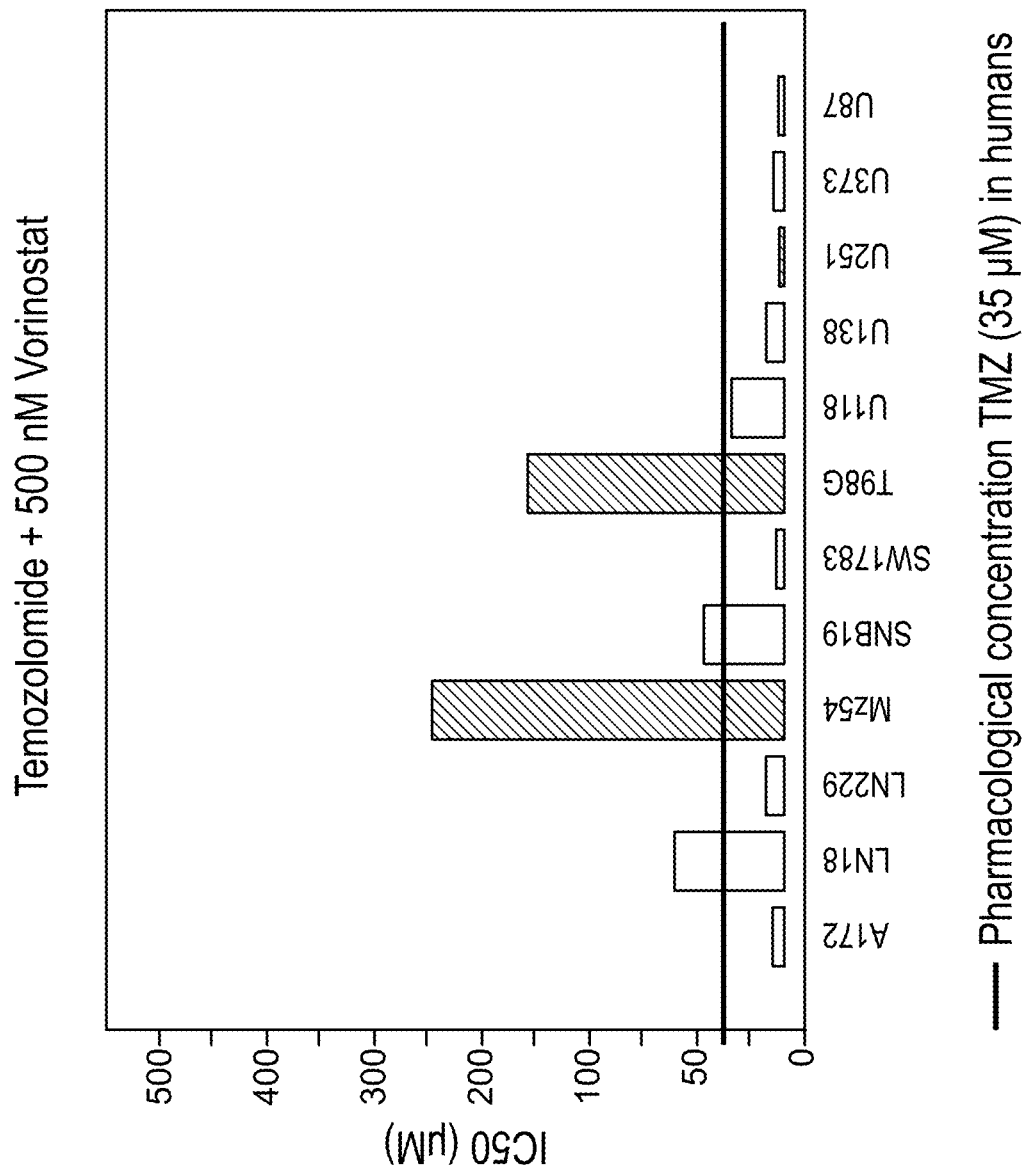
FIG. 3 is a plot of the $IC_{50}$ for the twelve tested GBM cell lines after temozolomide and vorinostat was administered.

In a separate experiment, TMZ was used in combination with 500 nM vorinostat. It is known that vorinostat is synergistic with TMZ in GBM cell lines. As can be seen from FIG. 3, while the MGMT positive GBM cell lines LN18 and U118 were sensitive to this combination, T98G and Mz54 were still very resistant. The $IC_{50}$ of T98G was reduced but it is not the range of achievable doses in humans.

Figure 4:
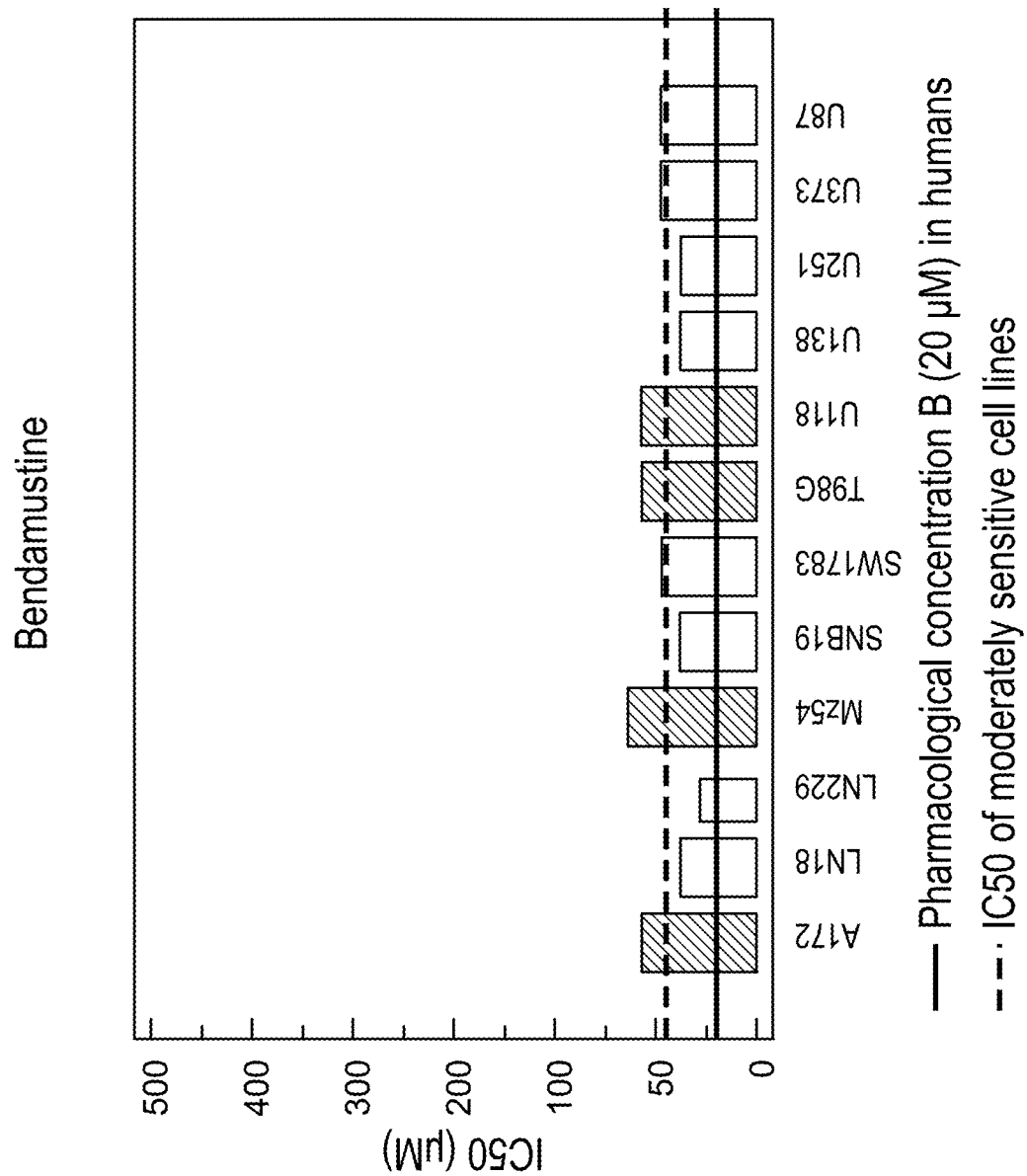
FIG. 4 is a plot of the $IC_{50}$ for the twelve tested GBM cell lines after bendamustine was administered.

FIG. 4 shows that none of the GBM cell lines were highly sensitive to bendamustine, while LN18, LN229, SNB19, U138, U251, U373, SW1783 and U87 GBM cell lines were moderately sensitive to bendamustine, while A172, Mz54, T98G and U118 were resistant to bendamustine.

Figure 5:
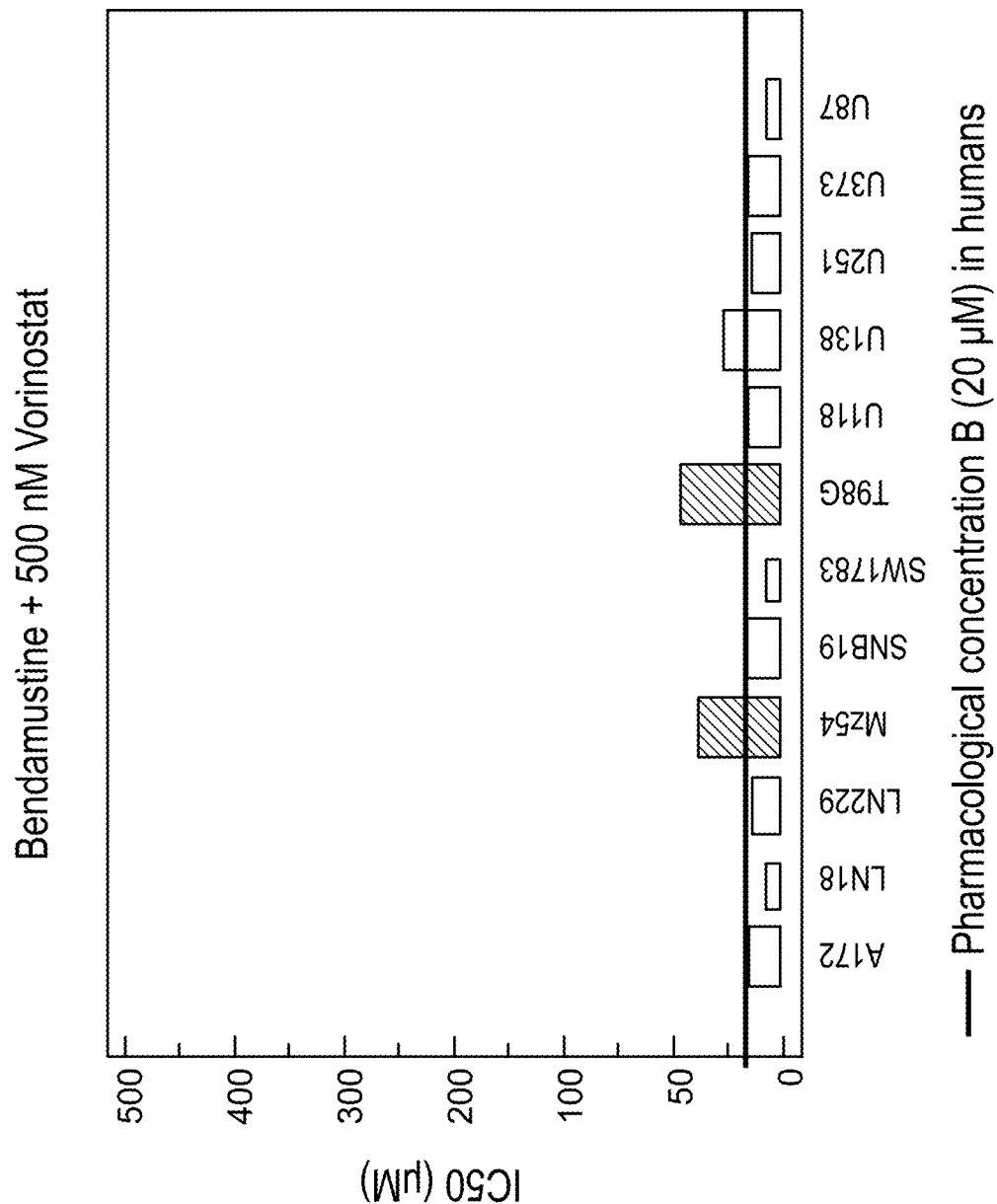
FIG. 5 is a plot of the $IC_{50}$ for the twelve tested GBM cell lines after bendamustine and vorinostat was administered.

As can be seen from FIG. 5, when bendamustine was combined with 500 nM vorinostat very similar results were achieved to those with TMZ and vorinostat, i.e. all cell lines were highly sensitive except Mz54 and T98G and while the $IC_{50}$ of T98G was reduced it is not the range of achievable doses in humans.

Figure 6:
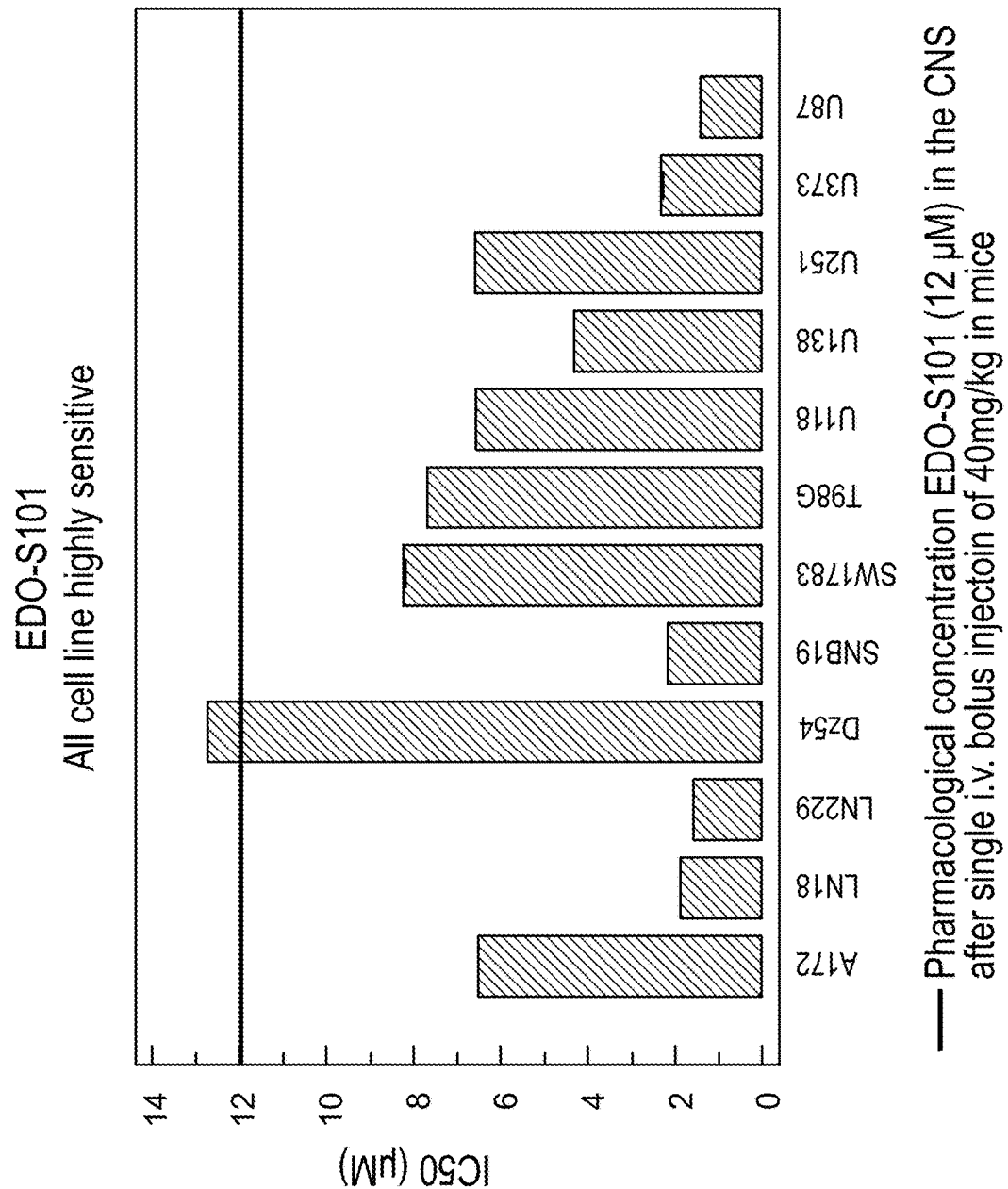
FIG. 6 is a plot of percentage of cell survival against concentration of EDO-S101 (µM) for each of the twelve tested cell lines.

In comparison to the other single compounds and combinations, the $IC_{50}$ curves for the twelve tested cell lines in FIG. 6 demonstrate that all twelve cell lines including all of the MGMT positive cell lines were highly sensitive to EDO-S101. This demonstrates that EDO-S101 is a highly promising therapeutic agent against both MGMT negative and MGMT positive GBMs.

A summary of the $IC_{50}$ values for the different cell lines is shown in the following Table 2.

TABLE 2

| Cell Line | Origin | Characteristics | Bendamustin | EDO-S101 | Temozolamide |
|---|---|---|---|---|---|
| U251MG | Sigma-Aldrich (09063001) | MGMT neg. | 30.0 | 6.60 | 20.0 |
| U87MG | ATCC (HTB-14) | MGMT neg. | 50.0 | 1.36 | 20.0 |
| T98G | ATCC CRL-1690 | MGMT pos. | 52.0 | 7.70 | >100 |
| U118MG | HTB-15 | MGMT pos. | 35.0 | 6.61 | >100 |
| U373MG (Uppsala) | Sigma-Aldrich (08061901) | MGMT neg. | 35.0 | 2.26 | 80.0 |
| Mz-54 | Goethe-University Frankfurt | MGMT pos. | 60.0 | 12.73 | >100 |

TABLE 2-continued

| Cell Line | Origin | Characteristics | Bendamustin | EDO-S101 | Temozolamide |
|---|---|---|---|---|---|
| A172 | CRL-1620 | MGMT neg. | 55.0 | 6.45 | ~100 |
| U138MG | ATCC (HTB-16) | MGMT pos. | 30.0 | 4.27 | >100 |
| LN228 | ATCC (CRL-2611) | MGMT neg | 35.0 | 1.55 | >100 |
| SW1783 | ATCC (HTB-13) | MGMT neg. | 38.0 | 8.24 | 80.0 |
| LN18 | ATCC (CRL-2610) | MGMT pos. | 25.0 | 1.87 | >100 |
| SNB19 | NCI | MGMT neg. | 32.0 | 2.17 | >100 |

Example 3 In Vivo Evaluation of EDO-S101 in Murine Models for Glioblastoma Multiforme Therapeutic activity of EDO-S101 was determined in murine brain tumour models against GBM, based on tumour growth as determined by bioluminescence imaging and survival analysis as determined by Kaplan-Meier analysis.

Murine brain tumour models were created by intracerebral injection of $3\times10^5$ luciferase-transfected GBM12 cells in athymic mice under aesthesia using a stereotactic platform. GBM12 is a MGMT negative tumour cell line. Eight-week-old athymic mice underwent minimum 7-day acclimation/quarantine prior to surgery. Surgery was performed in a laminar flow hood under sterile conditions. Tylenol 300 mg/kg PO was given for analgesia 24 hours before the surgery continuing 48 hours postoperatively. Aesthesia was achieved by inhalation of 1-2% isoflurane. After the mouse became well anesthetized, it was placed in the Kopf stereotactic instrument. A small amount of BNP antibiotic cream (a mixture of Bacitracin, Neomycin and Polymyxin) was smeared on its eyes to prevent infection and corneal damage during surgery. A strip of soft fabric was placed over the mouse's body and tail to prevent excessive heat loss during surgery. The scalp area was cleaned with a 2% solution of Betadine and dried with cotton tipped applicator. A midline sagittal incision was made in the scalp.

A small burr hole was drilled in the left skull with a surgical drill (Kopf) or a Dremel drill according to the coordinates (AP: 0.5 mm, LM: 2.5 mm) as determined by reference to the mouse brain atlas by Franklin and Paxinos. The dura mater was surgically exposed, and a 10 μl-Hamilton syringe with a 26S-gauge bevelled needle was lowered into the left cerebral hemisphere up to the depth of 3 mm and 5 μl of the $3\times10^5$ luciferase-transfected GBM12 cells tumour cells was slowly infused (0.5 μl/min). The needle was left in place for 5 minutes to prevent reflux and then slowly removed. The skin was closed with wound clips. After surgery, the mice recovered in a warm environment and returned to their cages when motor activity returned. Cages were placed on top of a heating pad to minimize the loss of body heat during the recovery. The mice were monitored post-operatively at least twice a day for 5 days or until recovery is complete. EDO-S101 (60 mg/kg body weight) or bendamustine (50 mg/kg body weight) were administered via the tail vein starting at day +4 post intracerebral tumour cell implantation and then subsequently at day +11 and day +18. Limb paralysis was taken as an endpoint for survival analysis.

After intracerebral injection of the GBM cells, all the mice were subjected to bioluminescence imaging (BLI) twice a week starting at day-4 post-intracerebral injection to monitor the real-time in vivo tumour growth. BLI was conducted using a Xenogen Lumina optical imaging system (Caliper Life Sciences, Hopkinton, MA). Mice were anesthetized with isoflurane before intraperitoneal injections of luciferin at a dose of 150 mg/kg, providing a saturating substrate concentration for luciferase enzyme. Peak luminescent signals were recorded 10 minutes after luciferin injection. Regions of interest encompassing the intracranial area of signal were defined using Living Image software (Xenogen, Alameda, CA), and the total photons/s/steradian/cm2 was recorded.

ANOVA was used to determine the statistical significance of the differences between experimental groups at each time point. Kaplan-Meier survival curves were generated using Prism4 software (GraphPad Software, LaJolla CA) and the statistical difference between curves was derived with a log-rank test. P<0.05 was considered significant.

Figure 7A:
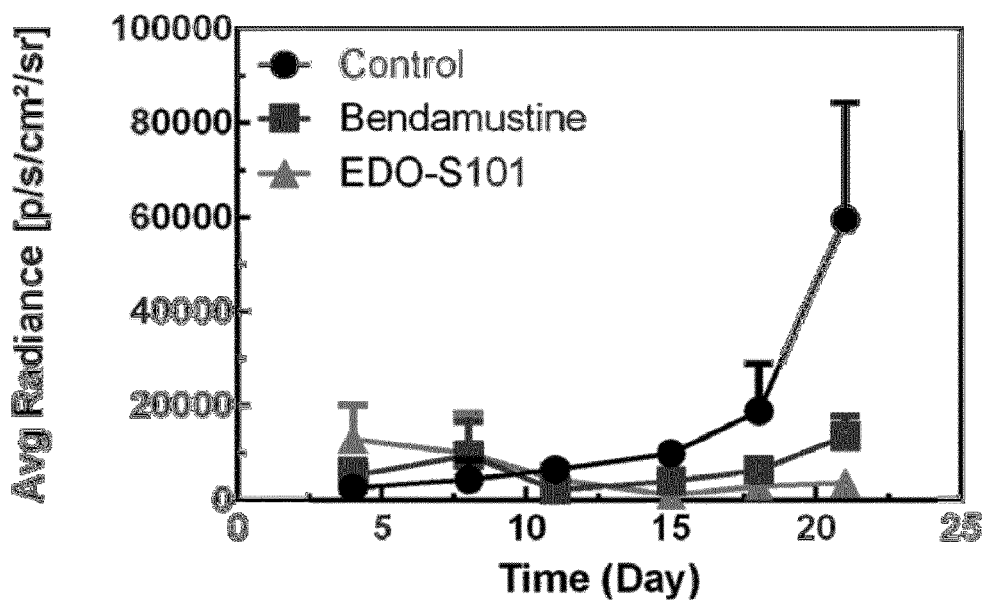
FIG. 7a is a plot of luminescence against time as a measure of growth of GBM12 cells post-injection.
Figure 7B:
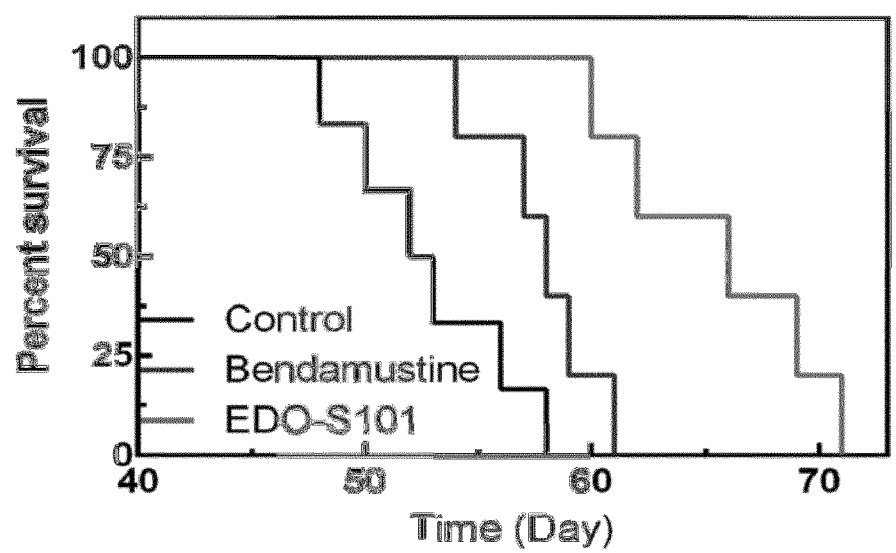
FIG. 7b is a plot of percent survival versus time showing the prolongation of survival for EDO-S101 against bendamustine and control.

In this patient-derived xenograft model for GBM (GBM12), EDO-S101 was administered at IV 60 mg/kg weekly on day +4, +11, +18 post intracerebral implantation of tumour cells (MTD dose). Bendamustine was given at IV 50 mg/kg weekly on day +4, +11, +18 (MTD dose). EDO-S101 was found to have significant therapeutic activity with suppression of tumour growth and prolongation of survival with median survival of 66 days compared to 58 days with Bendamustine, and 52 days in no-treatment controls (see FIGS. 7a and 7b). EDO-S101 has excellent therapeutic activity against this MGMT negative glioblastoma multiforme.

The above procedure was followed in similar manner using the cell lines U87G and U251G. Once again, EDO-S101 (60 mg/kg) was administered intravenously via the tail vein, but in these experiments it was administered at days 1, 8 and 15. In place of bendamustine, TMZ was administered as a comparison at 16 mg/kg for 5 consecutive days, po. The mice were sacrificed after 28 days.

Figure 8:
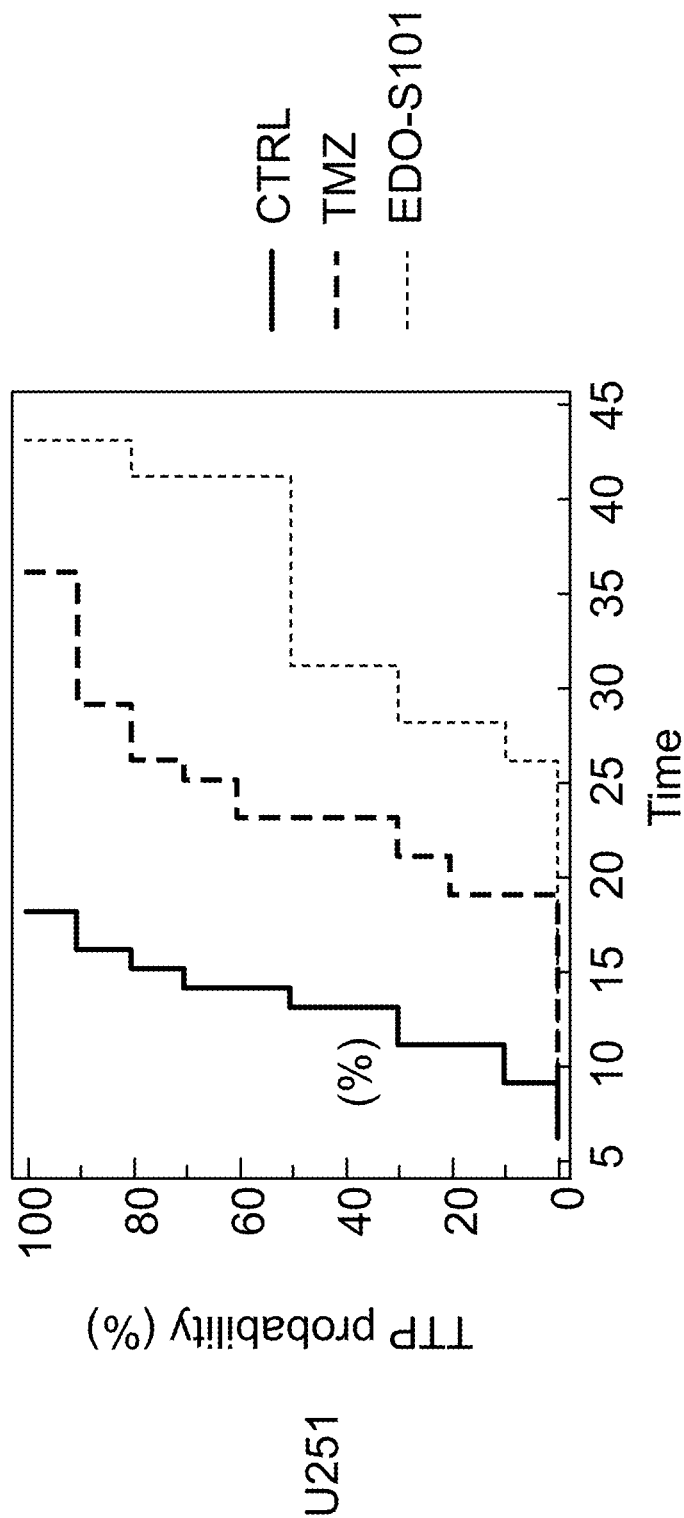
FIG. 8 is a plot of time to progression (TTP) probability (%) against time for mice having implanted U251 tumours treated with EDO-S101.
Figure 9:
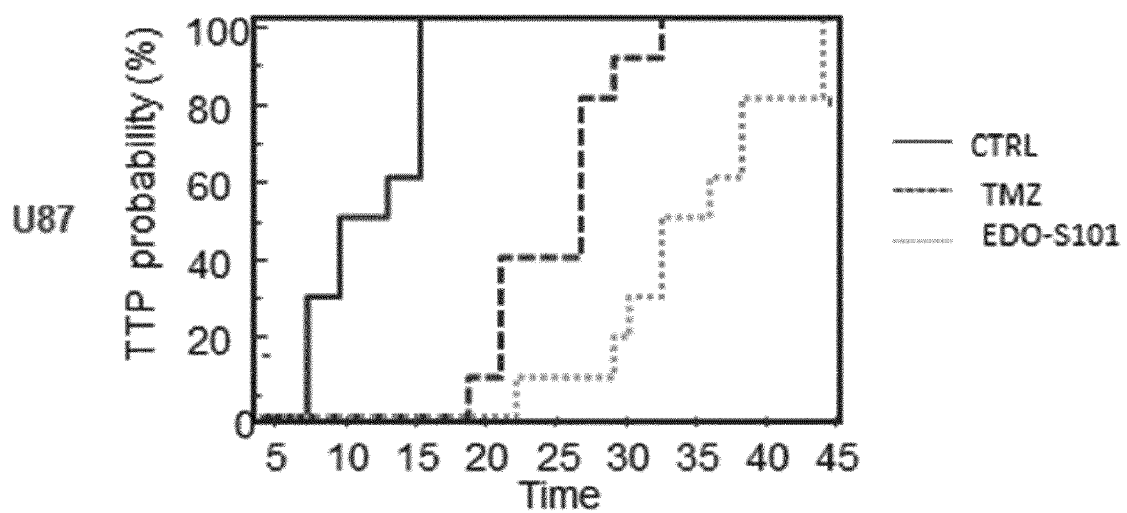
FIG. 9 is a plot of time to progression (TTP) probability (%) against time for mice having implanted U87 tumours treated with EDO-S101.

The plot of time to progression (TTP) probability (%) against time in FIG. 8 for mice having implanted U251 tumours shows that the TTP for the mice treated with EDO-S101 was significantly longer than that observed both for the control mice and those treated with TMZ. A similar significant increase in TTP was observed for mice having implanted U87 tumours, with EDO-S101 having a significantly longer TTP than both control and TMZ (see FIG. 9).

Example 4 In Vivo Evaluation of EDO-S101 (Alone or in Combination with Radiotherapy) in Murine Models for Glioblastoma Multiforme Against Radiotherapy and Temozolamide (Alone or in Combination In a first experiment, U251, U87 and T98G cell lines were treated with radiotherapy alone or with radiotherapy and EDO-S101.

For clonogenic survival, exponentially growing cells (70% confluence) were cultured in regular media and treated with EDO-S101 at the appropriate concentrations, or vehicle (final DMSO concentration of 0.1%) for 24 hr. Tumour cell irradiation was done using a 6 MV linear accelerator Elekta Synergy using a clinically calibrated irradiation field of 30×30 cm. Two cm thick plates of perspex were positioned above and below the cell culture flasks completely filled with medium to compensate for the build-up effect. Non-irradiated controls were handled identically to the irradiated cells with the exception of the radiation exposure. After treatment, cells were diluted at the appropriate concentration (1,000 cells) and re-seeded into a new 100 mm tissue culture dish (in triplicate) and incubated for 14 days. At day 14 the media was removed and colonies were fixed with methanol: acetic acid (10:1, v/v), and stained with crystal violet. Colonies containing more than 50 cells were counted. The plating efficiency (PE) was calculated as the number of colonies observed/the number of cell plated. The surviving fraction was calculated as the number of colonies formed in the treated dishes compared with the number formed in the control. The survival curves were analyzed using SPSS (Chicago, IL) statistical software by means of a fit of the data by a weighted, stratified, linear regression, according to the linear-quadratic formula: $S(D)/S(O)=\exp-(aD+bD2)$.

For the MGMT negative U251MG glioblastoma cell line, the $IC_{50}$ was measured to be 6.60 μM for EDO-S101 (compared to 30 μM for bendamustin and 20 μM for temozolamide).

For the MGMT negative U87G glioblastoma cell line, the $IC_{50}$ was measured to be 1.36 μM for EDO-S101 (compared to 50 μM for bendamustin and 20 μM for temozolamide).

For the MGMT positive T98G glioblastoma cell line, the $IC_{50}$ was measured to be 7.70 μM for EDO-S101 (compared to 52 μM for bendamustin and >100 μM for temozolamide).

Figure 10:
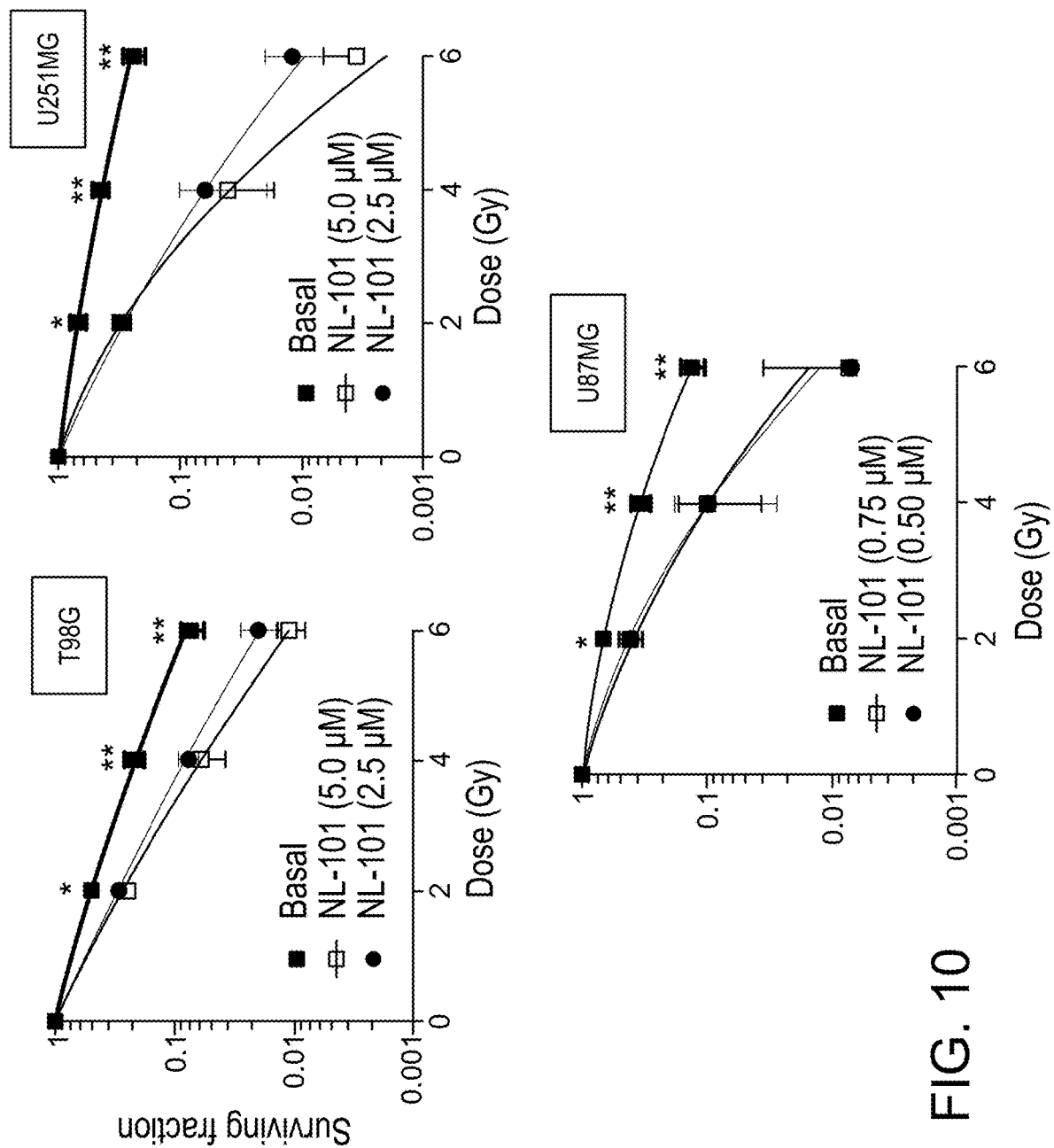
FIG. 10 is a plot of surviving fraction against the dose of radiotherapy (Gy) for U251, U87 and T98G cells treated with radiotherapy alone, radiotherapy and 2.5 µM EDO-S101 (shown as NL-101 in the figure) and 5 µM EDO-S101 EDO-S101.

As can be seen from FIG. 10, the % survival rate for the glioblastoma cells was considerably reduced when radiotherapy was used in combination with a dose of EDO-S101 (2.5 μM or 5 μM) compared to radiotherapy alone, in all 3 GBM cell lines.

Next, adopting the procedure of Example 3, s.c. xenograft models of GBMs in mice were prepared using the GBM cell lines U251 and U87.

The U251 mice prepared as above were subjected either subjected to radiotherapy (2 Gy for 5 consecutive days), treatment with EDO-S101 (60 mg/kg intravenously at days 1, 8 and 15 of the treatment cycle) or control only. Before any irradiation mice were anesthetized with a mixture of ketamine (25 mg/ml)/xylazine (5 mg/ml). Anesthetized tumor-bearing mice received a focal irradiation at the dose of 2 Gy for 5 consecutive days. Irradiation was delivered using an X-ray linear accelerator at a dose rate of 200 cGy/min at room temperature. All mice were shielded with a specially designed lead apparatus to allow irradiation to the right hind limb. Mice were kept under these conditions until all irradiation finished.

Figure 11:
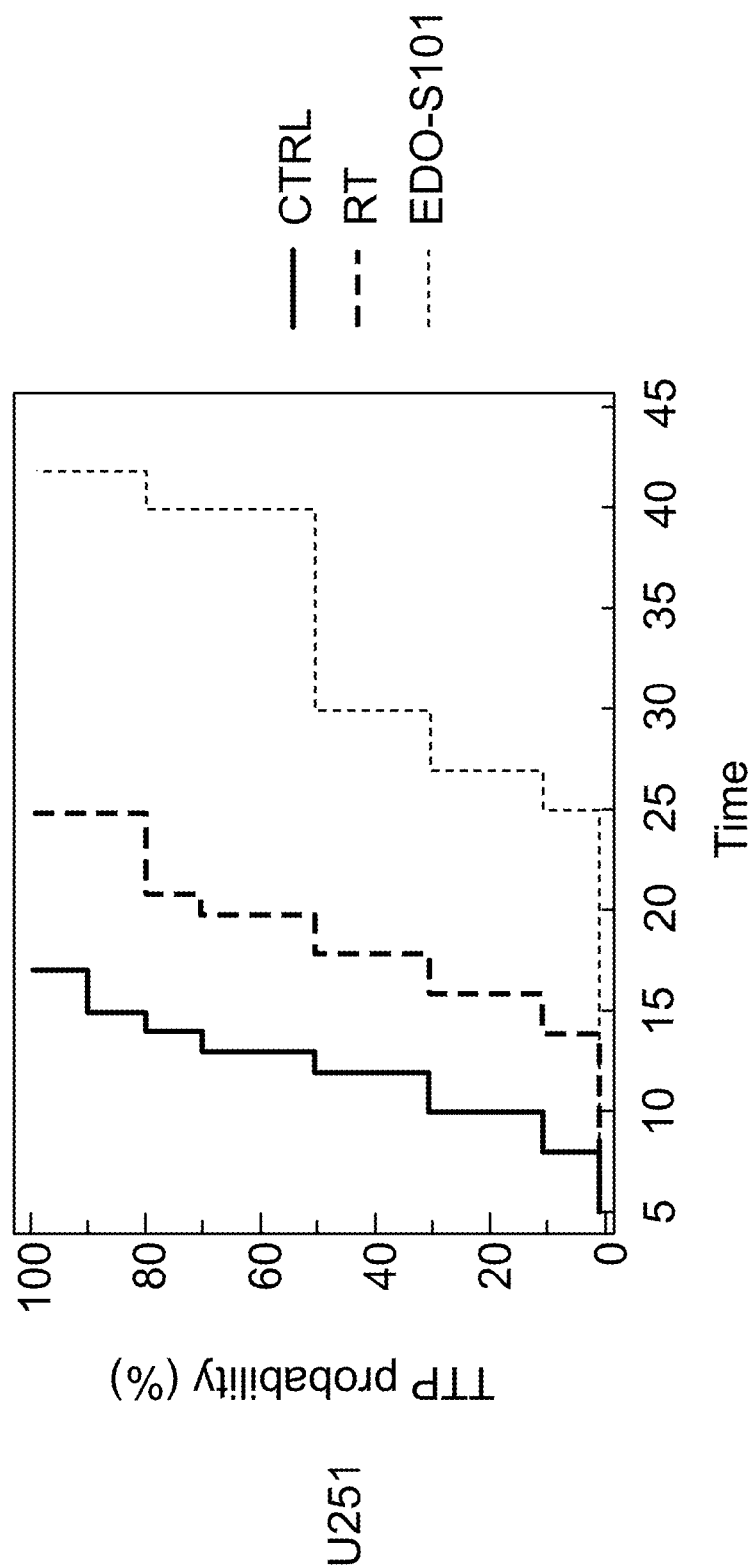
FIG. 11 is a plot of time to progression (TTP) probability (%) against time for mice having implanted U251 tumours treated with control, radiotherapy and EDO-S101.

A study was made of the progression of the GBM according to the procedure of Example 3. A plot of the time to progression probability (%) against time is shown in FIG. 11. From this, it is evident that the time to progression for the mice treated with EDO-S101 is considerably longer than observed for radiotherapy-treated tumours.

Figure 12:
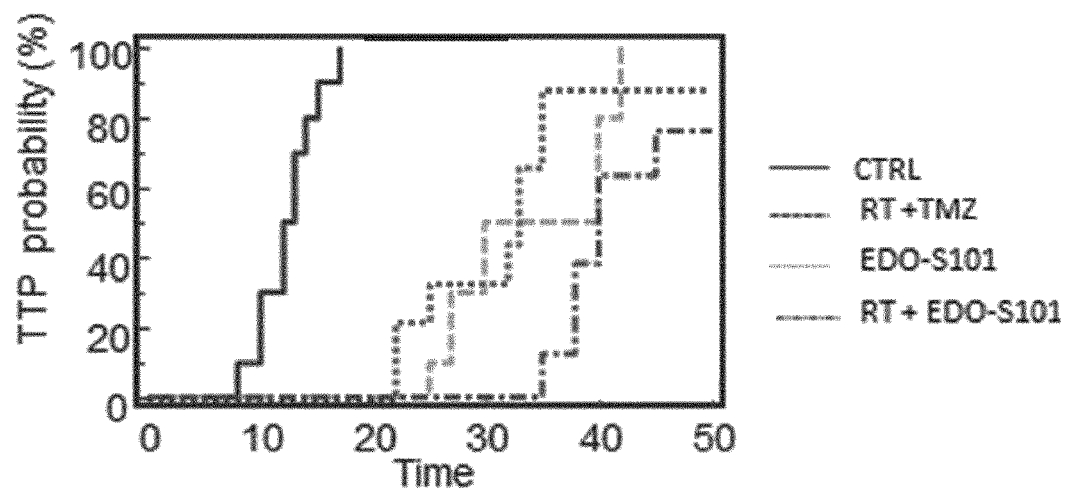
FIG. 12 is a plot of time to progression (TTP) probability (%) against time for mice having implanted U251 tumours treated with control, radiotherapy and temozolomide, EDO-S101, and Radiotherapy and EDO-S101.

In a follow up experiment, U251 mice prepared in the same manner were either subjected to the current gold standard treatment of radiotherapy and temozolamide (2 Gy for 5 consecutive days and 16 mg/kg for 5 consecutive days, po), treatment with EDO-S101 (60 mg/kg, intravenously at days 1, 8 and 15 of the treatment cycle), treatment with EDO-S101 and radiotherapy (2 Gy for 5 consecutive days and 60 mg/kg, intravenously at days 1, 8 and 15 of the treatment cycle) or control. A plot of the time to progression probability (%) against time is shown in FIG. 12. From this, it is evident that the time to progression for the mice treated with EDO-S101 and radiotherapy is significantly longer than that observed for tumours treated with EDO-S101 alone. Furthermore, the time to progression for the combination of radiotherapy and EDO-S101 was significantly longer than that observed for tumours treated with radiotherapy and temozolomide, the current gold standard treatment.

Figure 13:
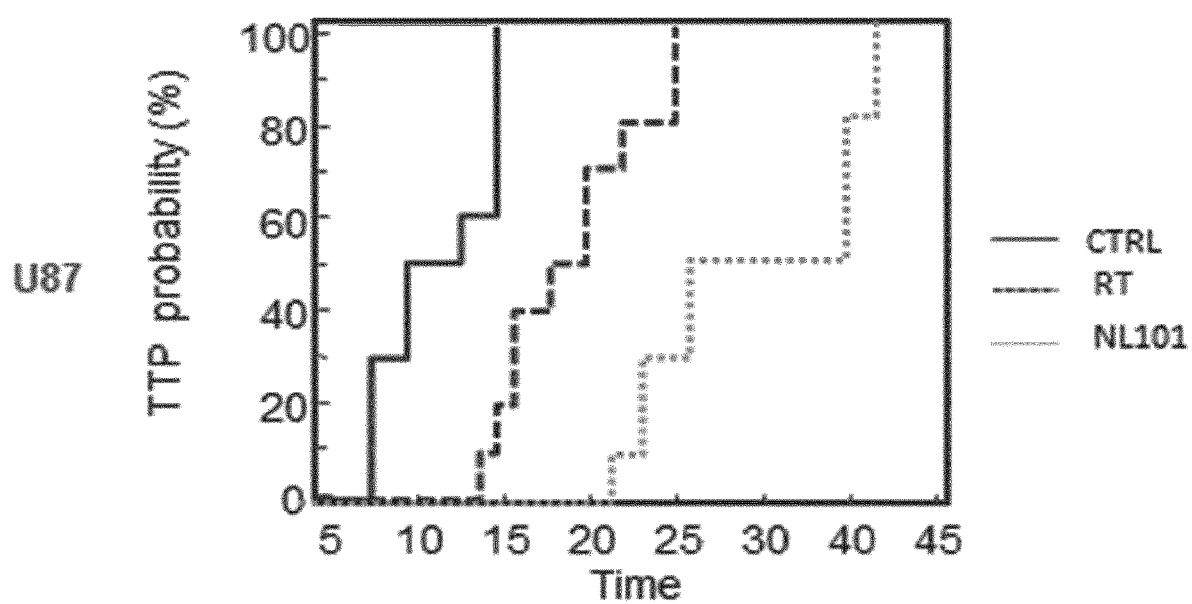
FIG. 13 is a plot of time to progression (TTP) probability (%) against time for mice having implanted U87 tumours treated with control, radiotherapy and EDO-S101.

The same sequence of experiments was followed, but this time with the s.c. xenograft models of GBM in mice prepared using the GBM cell line U87. In a first experiment, the U87 mice prepared as above were subjected either subjected to radiotherapy (2 Gy for 5 consecutive days), treatment with EDO-S101 (60 mg/kg intravenously at days 1, 8 and 15 of the treatment cycle) or control only. A study was made of the progression of the GBM. A plot of the time to progression probability (%) against time is shown in FIG. 13. From this, it is evident that the time to progression for the mice treated with EDO-S101 (referred to in FIG. 13 as NL101) is considerably longer than observed for radiotherapy treated tumours.

Figure 14:
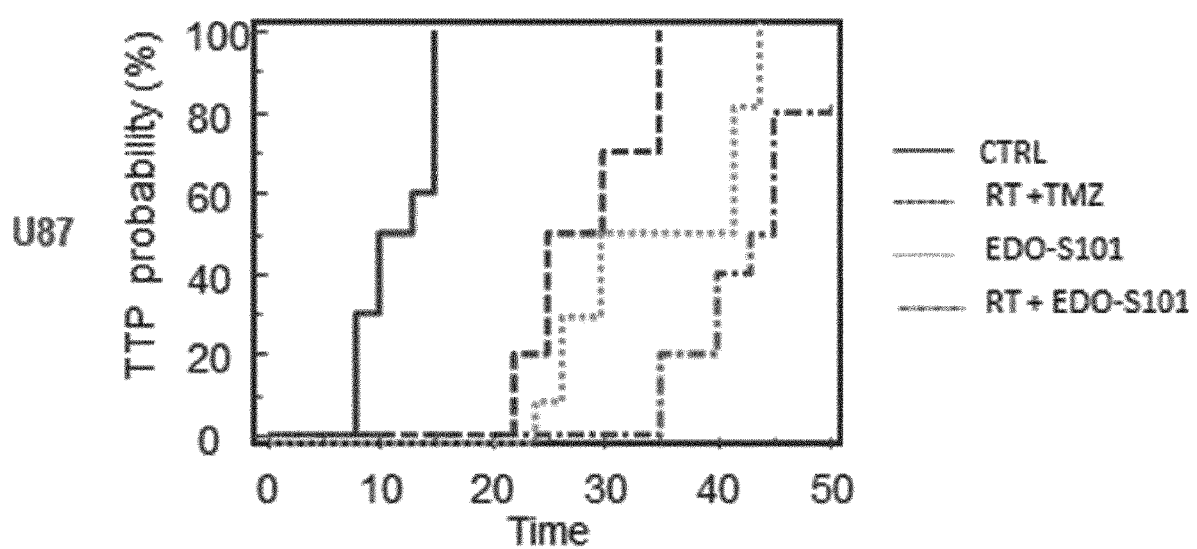
FIG. 14 is a plot of time to progression (TTP) probability (%) against time for mice having implanted U87 tumours treated with control, radiotherapy and temozolomide, EDO-S101, and radiotherapy and EDO-S101.

In a similar follow up experiment as that used for the U251 mice, U87 mice prepared in the same manner were either subjected to the current gold standard treatment radiotherapy and temozolomide (2 Gy for 5 consecutive days and 16 mg/kg for 5 consecutive days, po), treatment with EDO-S101 (60 mg/kg, intravenously at days 1, 8 and 15 of the treatment cycle), treatment with EDO-S101 and radiotherapy (2 Gy for 5 consecutive days and 60 mg/kg, intravenously at days 1, 8 and 15 of the treatment cycle) or control. A plot of the time to progression probability (%) against time is shown in FIG. 14. From this, it is evident that the time to progression for the mice treated with EDO-S101 and radiotherapy is significantly longer than that observed for tumours treated with EDO-S101 alone. Furthermore, the time to progression for the combination of radiotherapy and EDO-S101 was significantly longer that observed for radiotherapy and temozolomide, the current gold standard treatment. It should also be noted that the time to progression observed for the U87 mice treated with EDO-S101 alone was actually greater than that achieved with the combined radiotherapy and temozolomide treatment.

The time to progression of the tumours was increased from approximately 17-18 days for the control for the U251G mouse xenograft model, to 42 days with a combination of radiotherapy and temozolamide to over 50 days for EDO-S101 alone (significance P=0.924) to significantly over 50 days for a combination of EDO-S101 and radiotherapy (significance P=0.0359).

It was found that the time to progression of the tumours was increased from approximately 15 days for the control for the U87G mouse xenograft model, to 35 days with a combination of radiotherapy and temozolamide to 40 days for EDO-S101 alone (significance P=2372) to significantly over 50 days for a combination of EDO-S101 and radiotherapy (significance P=0.0001).

Example 5 Histological Evaluation of Tumours:
Orthotopic Model of U251-Luciferase Transfected Cells Mice isotopically transfected with U251-luciferase in accordance with the procedure of Example 3 were treated with radiotherapy (2 Gy for 5 consecutive days), temozolomide (16 mg/kg for 5 consecutive days, po), radiotherapy and temozolomide (2 Gy for 5 consecutive days and 16 mg/kg for 5 consecutive days, po), EDO-S101 (60 mg/kg, intravenously at days 1, 8 and 15 of the treatment cycle) or control vehicle.

Intracranial tumour growth was monitored with the Hamamatsu imaging system (Caliper Life Sciences, Hopkinton, MA, USA). Mice were anesthetized with 2% to 4% isofluorane (Baxter, Deerfield, IL, USA) followed by intraperitoneal injections of 150 mg/kg d-luciferin (In Vivo Imaging Solutions). Five animals were measured at the same time and the luminescent camera was set to 1 minute exposure, medium binning, 1 f/stop, blocked excitation filter, and open emission filter. The photographic camera was set to 2 s exposure, medium binning, and 8 f/stop. The field of view was set to 22 cm to capture five mice at once. Serial images were taken on a weekly basis using identical settings. Bioluminescence intensity was quantified using the Living Image software (Caliper Life Sciences).

Before any irradiation mice were anesthetized with a mixture of ketamine (25 mg/ml)/xylazine (5 mg/ml). Anesthetized tumour-bearing mice received a focal irradiation at the dose of 2 Gy for 5 consecutive days. Irradiation was delivered using an X-ray linear accelerator at a dose rate of 200 cGy/min at room temperature. All mice were shielded with a specially designed lead apparatus to allow irradiation to the right hind limb. Mice were kept under these conditions until all irradiation finished.

All images were obtained in the transverse plane using the following sequences: transverse T2-weighted turbo spin-echo (TSE) sequence (repetition time [TR] msec/echo time [TE] msec) 6766/120, number of signal acquired 4, matrix of 192×192) applied with a section thickness of 0.9 mm, an intersection gap of 0.0 mm, and a flip angle of 160°. The field of view was 36×60 mm$^2$, which included the tumour in its entirety with a resultant voxel size of 0.3×0.3×1.0 mm$^3$.

Continuous variables were summarized as mean and standard deviation (SD) or as median and 95% CI for the median. For continuous variables not normally distributed, statistical comparisons between control and treated groups were established by carrying out the Kruskal-Wallis Tests. For continuous variables normally distributed, statistical comparisons between control and treated groups were established by carrying out the ANOVA test or by Student t test for unpaired data (for two comparisons).

Figure 15:
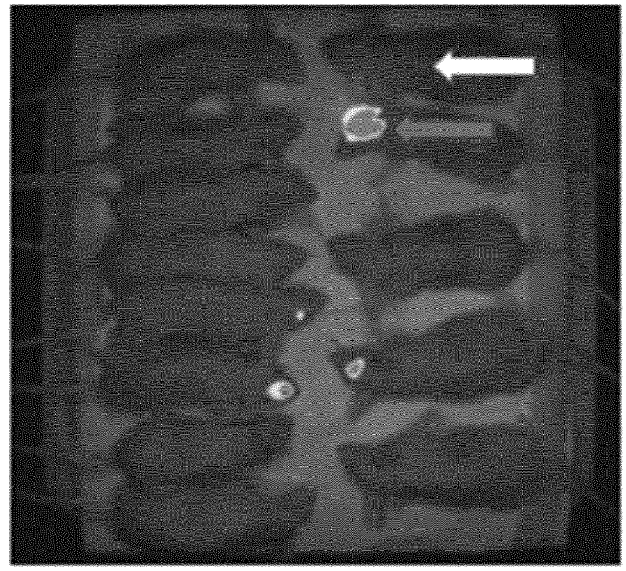
FIGS. 15 and 16 are bioluminescence images of orthotopic luciferase-transfected U251 GBM mice, after treatment with control vehicle, EDO-S101, temozolomide, and radiotherapy and temozolomide.
Figure 15:
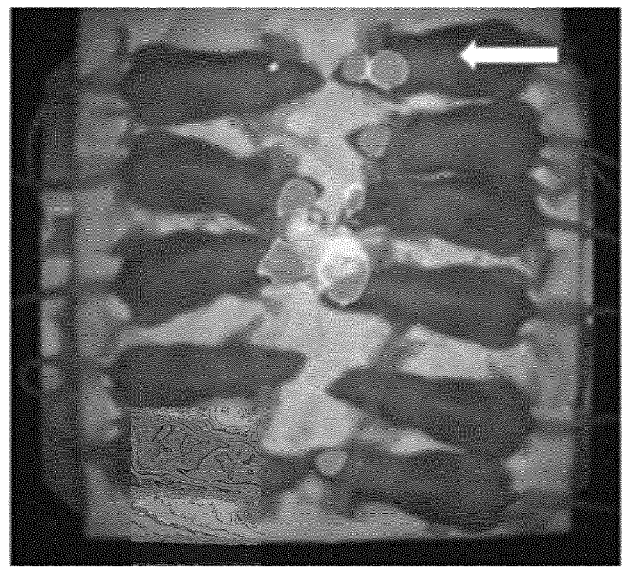
Figure 16:
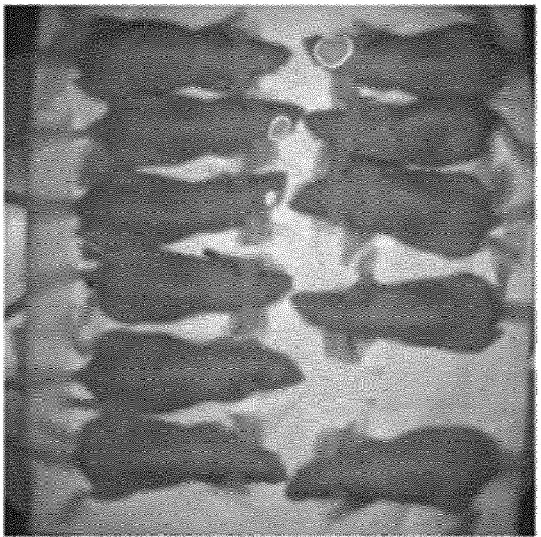
Figure 16:
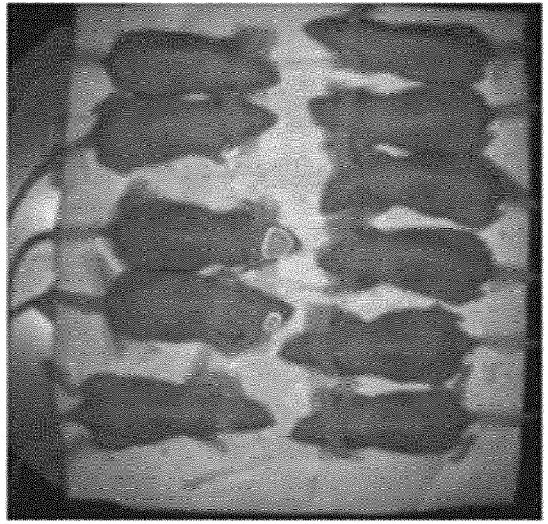

50 days after beginning of the different treatment regimes, the mice were sacrificed and the final intracranial lesions were visualized in the mice subjected to treatment with the control, EDO-S101, temozolomide, and radiotherapy and temozolomide. The results are shown in FIGS. 15 and 16. Similar results were achieved with both the EDO-S101 and temozolomide studies, both showing 5 out of 13 mice with tumours of some grade (38.5%) compared to 8 out of 11 (72.7%) in the control. However, only 1 of the 13 of the EDO-S101 treated mice displayed a large lesion, while 2 of the 13 temozolomide treated mice displayed large lesions. In the radiotherapy and temozolomide study, only 2 of the 11 mice (18.2%) displayed lesions at the end of the study, although both of these were large lesions. It can be concluded from this that EDO-S101 is highly effective in preventing spread of GBMs.

Figure 17:
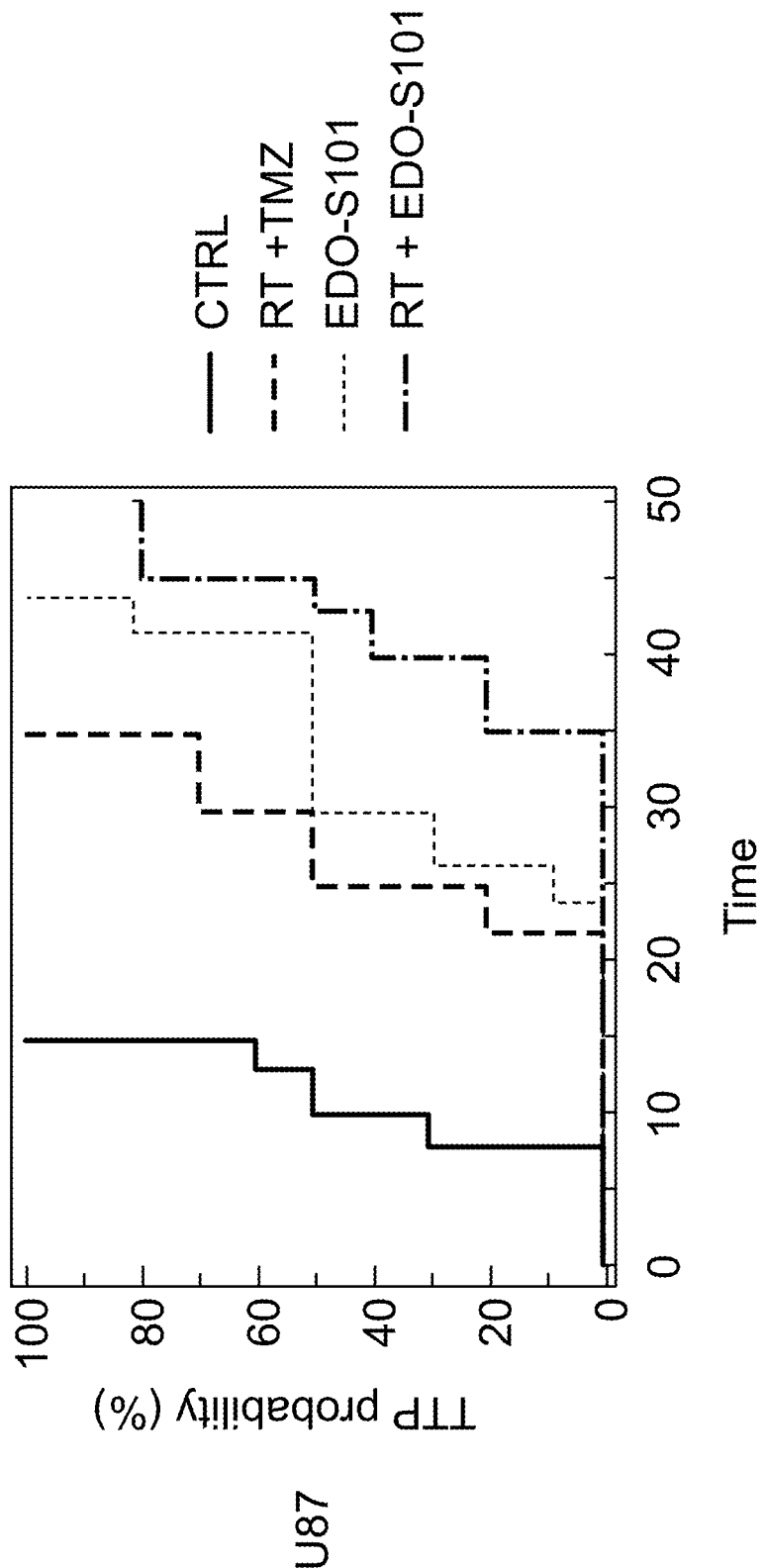
FIG. 17 is a plot of survival probability (%) against time for orthotopic luciferase-transfected U251 GBM mice, after treatment with control vehicle, radiotherapy, EDO-S101, temozolomide, and radiotherapy and temozolomide.

The effectiveness of EDO-S101 in preventing spread of GBMs is further emphasized in FIG. 17, showing a plot of survival probability (%) against time (days). The survival probability for the mice treated with EDO-S101 was significantly greater than that for those treated with either radiotherapy or temozolomide. Only the mice treated with a combination of radiotherapy and temozolomide showed a higher overall survival probability than EDO-S101 alone.

Figure 18:
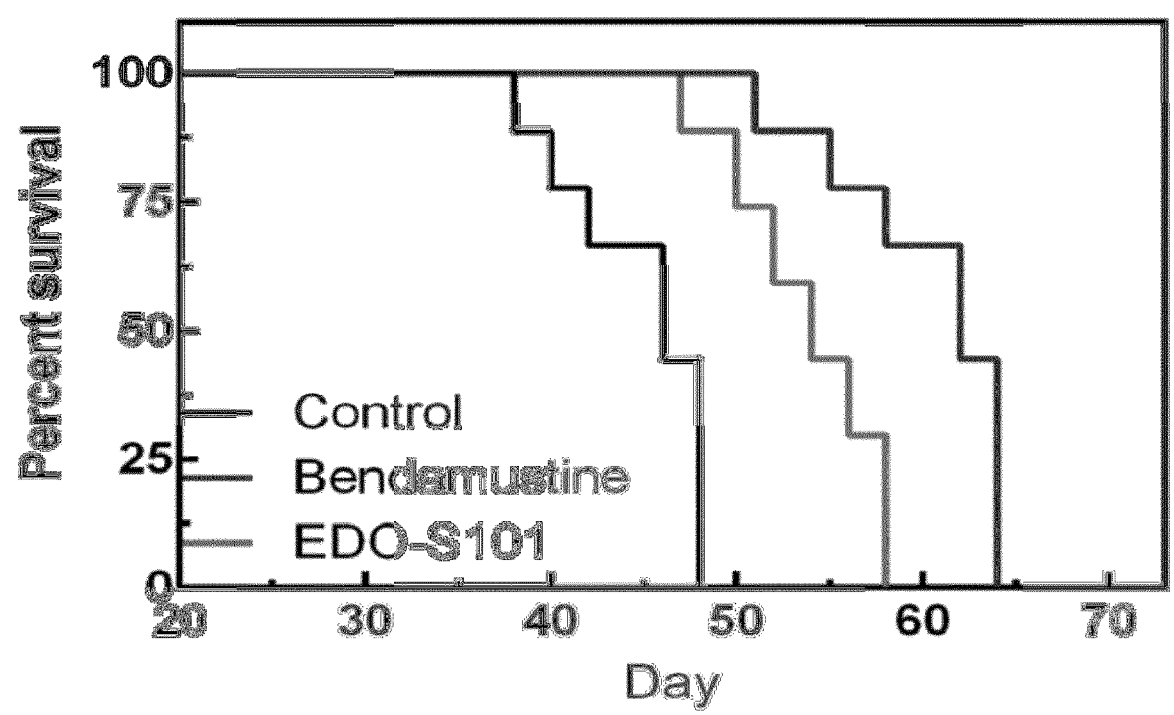
FIG. 18 is a plot of percent survival against time for mice having implanted OCI-LY10 CNS lymphomas treated with control, bendamustine and EDO-S101.

Example 6 In Vivo Evaluation of EDO-S101 in Murine Models for Primary CNS Lymphoma The procedure of Example 3 was repeated, except the murine models were created with 1×10$^5$ luciferase-transfected OCI-LY10B lymphoma cells to create a model of primary CNS lymphoma. EDO-S101 (60 mg/kg body weight), bendamustine (50 mg/kg body weight) and control was administered intravenously via a tail vein to separate groups of the test mice on days +4, +11 and +18 post intracerebral implantation of the OCI-LY10B lymphoma cells. Both EDO-S101 and bendamustine significantly suppressed tumour growth and prolonged the survival with median survival of 62 days and 54 days respectively compared to 48 days in no-treatment controls (see FIGS. 18a and 18b). EDO-S101 therefore appears to be a promising treatment for primary CNS lymphoma.

Figure 19:
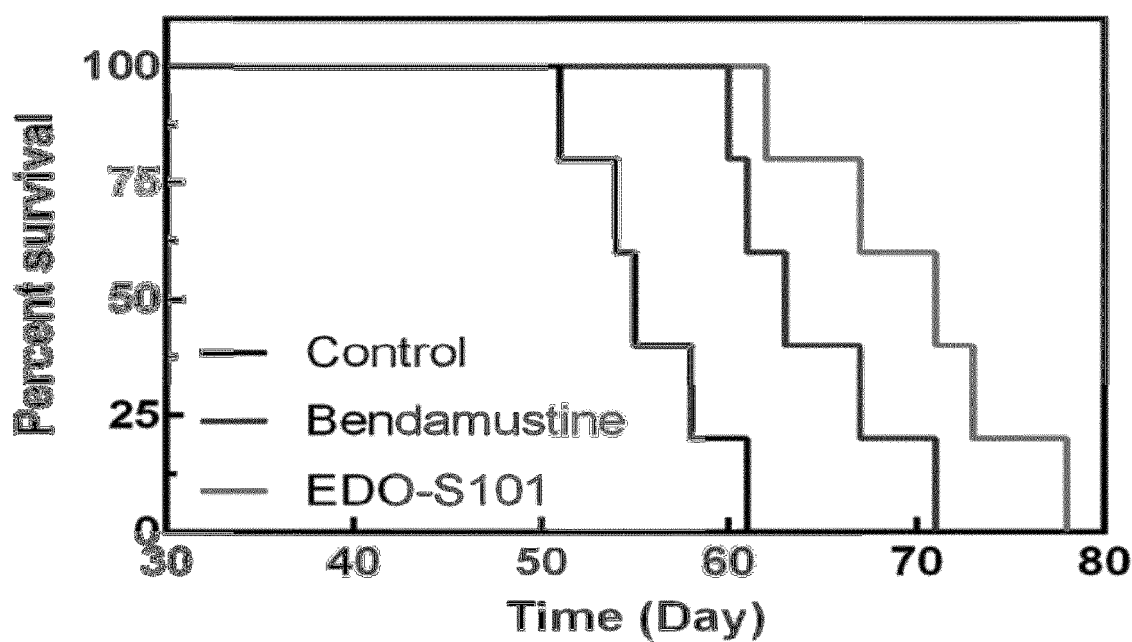
FIG. 19 is a plot of percent survival against time for mice having triple negative metastatic breast cancer of the brain after transfection with MB-468 breast cancer cells treated with control, bendamustine and EDO-S101.

Example 7 In Vivo Evaluation of EDO-S101 in Murine Models for Triple Metastatic Breast Cancer of the Brain The procedure of Example 3 was repeated, except the murine models were created with 1×10$^5$ luciferase-transfected MB-468 breast cancer cells to create a model of primary CNS lymphoma. EDO-S101 (60 mg/kg body weight), bendamustine (50 mg/kg body weight) and control was administered intravenously via a tail vein to separate groups of the test mice in a single dose on day +4 post intracerebral implantation of the MB-468 breast cancer cells. EDO-S101 showed significant therapeutic activity with suppression of tumour growth and prolongation of survival with median survival of 71 days compared to 62 days for bendamustine and 55 days for no-treatment controls (see FIGS. 19a and 19b). EDO-S101 therefore appears to be a particularly promising treatment for metastatic brain cancer.

In conclusion, the experiments demonstrate that the ability of EDO-S101 to pass through the blood-brain barrier is very good. This makes it a promising candidate for treatment of brain cancers. The experimental data further shows that it is active not only against MGMT negative GBMs but also MGMT positive GBMs, making it highly promising as a therapeutic for treatment of MGMT positive GBMs and other MGMT positive astrocytic brain tumours as no therapy has yet been developed for these. It also shows that it significantly prolongs median survival in cases of both primary CNS lymphoma and metastatic brain cancers, again making it a very promising therapeutic candidate for both conditions. The data also show that when EDO-S101 is administered in combination with radiotherapy then it shows significantly improved activity compared to EDO-S101 alone in the treatment of GBM.

The invention claimed is:
1. A method of treating an O$^6$-methylguanine-DNA methyltransferase (MGMT) positive Glioblastoma Multiforme (GBM) in a patient in need thereof, the method comprising administering to said patient a compound of formula I or a pharmacologically acceptable salt thereof:

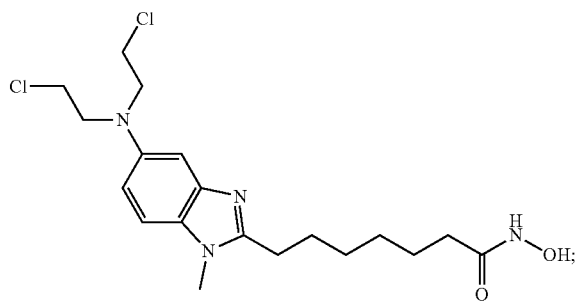

wherein the patient has received a surgery treatment followed by a treatment of temozolomide (TMZ).

2. The method according to claim 1, wherein the pharmacologically acceptable salt of the compound of formula I is a hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate or acetate salt.

3. The method according to claim 1, wherein the compound of formula I or pharmacologically acceptable salt thereof is administered intravenously to the patient in need thereof at a dosage level of from 0.1 mg/kg to 70 mg/kg body weight patient.

4. The method according to claim 3, wherein the compound of formula I or pharmacologically acceptable salt thereof is administered intravenously to the patient in need thereof at a dosage level of from 0.5 mg/kg to 50 mg/kg body weight patient.

5. The method according to claim 3, wherein the compound of formula I or pharmacologically acceptable salt thereof is administered intravenously to the patient in need thereof on day 1 only of a treatment cycle.

6. The method according to claim 1, wherein the patient in need thereof has received a treatment of radiotherapy.

7. The method according to claim 6, wherein said radiotherapy is given to the patient in need thereof at a dose of 1 to 5 Gy over 5 consecutive days.

* * * * *